US010890524B2

(12) United States Patent
Kusters

(10) Patent No.: US 10,890,524 B2
(45) Date of Patent: Jan. 12, 2021

(54) DISCERNING BETWEEN THE PRESENCE OF RED BLOOD CELLS AND FREE HEMOGLOBIN IN A BIOLOGICAL FLUID

(71) Applicant: Fenwal, Inc., Lake Zurich, IL (US)

(72) Inventor: Benjamin E. Kusters, Pleasant Prairie, WI (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/429,128

(22) Filed: Jun. 3, 2019

(65) Prior Publication Data

US 2019/0369008 A1 Dec. 5, 2019

Related U.S. Application Data

(60) Provisional application No. 62/680,653, filed on Jun. 5, 2018.

(51) Int. Cl.
*G01N 21/25* (2006.01)
*A61M 1/36* (2006.01)
(Continued)

(52) U.S. Cl.
CPC ......... *G01N 21/255* (2013.01); *A61M 1/3693* (2013.01); *G01N 21/359* (2013.01);
(Continued)

(58) Field of Classification Search
CPC ............. G01N 21/255; G01N 21/3577; G01N 21/359; G01N 33/49; G01N 2201/061; G01N 2201/062; G01N 33/491; G01N 21/35; A61M 1/3693; A61M 2202/0415; A61M 2202/0429; A61M 2202/0433;
(Continued)

(56) References Cited

U.S. PATENT DOCUMENTS

| | | | |
|---|---|---|---|
| 5,316,667 | A | 5/1994 | Brown et al. |
| 5,462,416 | A | 10/1995 | Dennehey et al. |

(Continued)

FOREIGN PATENT DOCUMENTS

WO WO2017/048673 A1 3/2017

OTHER PUBLICATIONS

Thorlabs, CCS Series Operational Manual, 2014, Manual, 1-6 (Year: 2014).*

(Continued)

*Primary Examiner* — Michael P LaPage
(74) *Attorney, Agent, or Firm* — Cook Alex Ltd.

(57) ABSTRACT

An optical sensor device includes a light source configured to emit a light including a wavelength in a range of 650 to 900 nm that is exposed to a biological fluid at first and second times. At least a portion of the light is reflected off of the fluid and received by a light detector. The light detector analyzes at least a portion of the received light to determine a first intensity of the light at the wavelength at the first time and a second intensity of the light at the wavelength at the second time. A controller compares the first and second intensities and generates an output indicative of the presence of red blood cells or free hemoglobin in the biological fluid depending on which intensity is greater and whether there is more redness in the biological fluid at the first time or at the second time.

20 Claims, 11 Drawing Sheets

(51) Int. Cl.
*G01N 21/3577* (2014.01)
*G01N 21/359* (2014.01)
*G01N 33/49* (2006.01)

(52) U.S. Cl.
CPC ......... *G01N 21/3577* (2013.01); *G01N 33/49* (2013.01); *A61M 2202/0415* (2013.01); *A61M 2202/0429* (2013.01); *A61M 2202/0433* (2013.01); *A61M 2205/3303* (2013.01); *A61M 2205/3306* (2013.01); *A61M 2205/3313* (2013.01); *G01N 2201/061* (2013.01)

(58) Field of Classification Search
CPC .. A61M 2205/3303; A61M 2205/3306; A61M 2205/3313; A61B 5/7246; A61B 5/14546; A61B 5/14557
See application file for complete search history.

(56) References Cited

U.S. PATENT DOCUMENTS

| | | | | |
|---|---|---|---|---|
| 5,632,893 | A | 5/1997 | Brown et al. | |
| 5,868,696 | A | 2/1999 | Giesler et al. | |
| 5,980,760 | A | 11/1999 | Min et al. | |
| 6,312,607 | B1 | 11/2001 | Brown et al. | |
| 7,011,761 | B2 | 3/2006 | Muller | |
| 7,297,272 | B2 | 11/2007 | Min et al. | |
| 9,164,078 | B2 | 10/2015 | Min et al. | |
| 9,833,557 | B2 | 12/2017 | Thill et al. | |
| 9,895,482 | B2 | 1/2018 | Kusters et al. | |
| 2003/0070969 | A1 | 4/2003 | Muller et al. | |
| 2008/0020481 | A1* | 1/2008 | Yamamoto | G01N 33/86 436/164 |
| 2011/0076695 | A1* | 3/2011 | Ohshiro | G01N 21/78 435/7.9 |
| 2013/0301901 | A1* | 11/2013 | Satish | G06T 7/0012 382/134 |
| 2013/0324815 | A1 | 12/2013 | Jian et al. | |
| 2014/0057771 | A1 | 2/2014 | Case et al. | |
| 2014/0128838 | A1* | 5/2014 | Satish | G06T 7/0012 604/503 |
| 2015/0219558 | A1 | 8/2015 | Koudelka et al. | |
| 2016/0366876 | A1* | 12/2016 | Min | A61M 1/3696 |

OTHER PUBLICATIONS

Extended European Search Report from the European Patent Office for European Application No. 19177867.9, dated Sep. 18, 2019 (10 Pages).

* cited by examiner

DISCERNING BETWEEN THE PRESENCE OF RED BLOOD CELLS AND FREE HEMOGLOBIN IN A BIOLOGICAL FLUID

CROSS-REFERENCE TO RELATED APPLICATIONS

This application claims the benefit of and priority of U.S. Provisional Patent Application Ser. No. 62/680,653, filed Jun. 5, 2018, the contents of which are incorporated by reference herein.

BACKGROUND

Field of the Disclosure

The present disclosure relates to optical detection of redness in biological fluid. More particularly, the present disclosure relates to differentiation of redness in biological fluid caused by the presence of red blood cells and redness caused by the presence of free hemoglobin.

Description of Related Art

Various blood processing systems now make it possible to collect particular blood constituents, instead of whole blood, from a blood source such as, but not limited to, a container of previously collected blood or other living or non-living source. Typically, in such systems, whole blood is drawn from a blood source, the particular blood component or constituent is separated, removed, and collected. The remaining blood constituents may be returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., which is an affiliate of Fresenius Kabi AG of Bad Homburg, Germany, or other centrifugal separation devices, or a spinning membrane-type separator, such as the AUTOPHERESIS-C® and AURORA® devices from Fenwal, Inc.

Systems of this type typically include one or more optical devices for monitoring the composition of the blood or a component thereof. One common approach to non-invasive blood and blood constituent analysis is based on the amount of light transmitted through the fluid. Different blood constituents absorb different wavelengths of light to different degrees, which may be used to determine certain characteristics of a fluid. However, light transmission through fluid containing even low quantities of red blood cells (i.e., fluids having a relatively low hematocrit) may be minimal due to significant scattering of the light. Another possible disadvantage of such transmission-based approaches is that they require access to opposing sides of a fluid path, which may not be available for certain fluid paths in certain systems.

U.S. Pat. No. 9,164,078 (which is hereby incorporated herein by reference) describes a system in which hematocrit of whole blood may be predicted using infrared light. The hematocrit of whole blood is useful information to have for an apheresis system and method because it indicates the red blood cell and plasma quantities available for collection, while the hematocrit of a separated blood component indicate the purity of a component that should contain red blood cells or the contamination of a component that should be free of red blood cells. Furthermore, when mononuclear cells are to be collected, the hematocrit of fluid exiting a separation device may be indicative of the quantity of mononuclear cells exiting the separation device.

The optical devices of these systems may also be configured for measuring the concentration of free hemoglobin of a constituent fluid. Hemoglobin is an iron-containing protein found in red blood cells, which functions to carry oxygen to the various body tissues. If a red blood cell is damaged (e.g., during separation of whole blood), the hemoglobin may leak out of the red blood cell as free hemoglobin. Reliable measurement of free hemoglobin concentration of a fluid is, thus, useful in determining whether red blood cells are being damaged (e.g., during blood separation). U.S. Pat. No. 9,833,557 (which is hereby incorporated herein by reference) describes an exemplary system in which the concentration of free hemoglobin in separated plasma may be determined, followed by the determination of an amount of free hemoglobin in a concentrated fluid separated from the plasma.

Conventional approaches to free hemoglobin detection involve the measurement of red and green light transmitted through a fluid. While such techniques are capable of producing reliable results, they may be susceptible to disturbances, such as when air bubbles are present in the fluid. When light being transmitted through a fluid encounters air bubbles, the light is scattered, which reduces the amount of light transmitted through the fluid to a light detector and may lead to erroneous measurements. Additionally, plasma or supernatant obtained from a product after separation or during storage is conventionally evaluated using specific free hemoglobin measurement assays, which may be time-consuming and costly. Further, as noted above, it may be impracticable to access opposing sides of a fluid-containing vessel, as required for transmission-based approaches.

In addition to determining the hematocrit or free hemoglobin concentration of a biological fluid, it may be advantageous to determine whether the redness of the fluid is due to the presence of red blood cells or free hemoglobin. Typically, whether the cause of redness in the fluid is due to the presence of red blood cells or free hemoglobin is predictable in view of a number of factors, which may include the nature of the fluid, the location of the portion or vessel being monitored with respect to the separation device, and the nature of the separation device. For example, when monitoring the plasma or supernatant outlet line of a "spinning membrane"-type separator (such as one of the type described in U.S. Pat. No. 9,895,482 and PCT Patent Application Publication No. WO 2017/048673 A1, both of which are hereby incorporated herein by reference), it is expected that the fluid will be free of cellular blood components (including red blood cells), such that any redness of the fluid will typically be attributable to the presence of free hemoglobin. Conversely, when monitoring the low density outlet of a centrifuge of the type described in U.S. Pat. No. 5,868,696 (which is hereby incorporated herein by reference), the incidence of contamination by red blood cells is more common than hemolysis, such that any redness of the fluid will typically be due to the presence of red blood cells. However, in both cases, while the cause of redness is predictable, it is possible in both cases for the redness to be caused by either the presence of red blood cells or free hemoglobin (e.g., if mechanical failure of a "spinning membrane"-type separator causes red blood cells to leak into the plasma or supernatant line). The presence of red blood cells versus free hemoglobin may be remedied by different approaches, such that it would be advantageous to determine which is the cause of redness in a fluid.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method of determining a cause of redness in a biological fluid includes exposing a biological fluid to a light including a wavelength in a range of 650 nm to 900 nm at a first time and at a second time that is subsequent to the first time so as to cause at least a portion of the light to be reflected by the biological fluid. At least a portion of the reflected light is received at the first time and at the second time, with at least a portion of the received light being analyzed at the first time to determine a first intensity of said at least a portion of the received light at said wavelength and at the second time to determine a second intensity of said at least a portion of the received light at said wavelength. It is also determined whether the redness in the biological fluid at the second time is greater or less than the redness in the biological fluid at the first time. The first intensity is compared to the second intensity and an output indicative of a presence of red blood cells in the biological fluid or of a presence of free hemoglobin in the biological fluid is generated, based upon the determination of whether the redness in the biological fluid at the second time is greater or less than the redness in the biological fluid at the first time and upon the comparison of the first intensity to the second intensity In another aspect, an optical sensor device includes a light source, a light detector, and a controller. The light source is configured to emit a light including a wavelength in a range of 650 nm to 900 nm, with at least a portion of the light being exposed to a biological fluid and reflected at a first time and at a second time that is subsequent to the first time. The light detector is configured to receive at least a portion of the reflected light and analyze at least a portion of the received light at the first time to determine a first intensity of said at least a portion of the received light at said wavelength and at the second time to determine a second intensity of said at least a portion of the received light at said wavelength. The controller is configured to compare the first intensity to the second intensity and generate an output indicative of a presence of red blood cells in the biological fluid or generate an output indicative of a presence of free hemoglobin in the biological fluid, based upon whether the redness in the biological fluid at the second time is greater or less than the redness in the biological fluid at the first time and upon said comparison of the first intensity to the second intensity.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
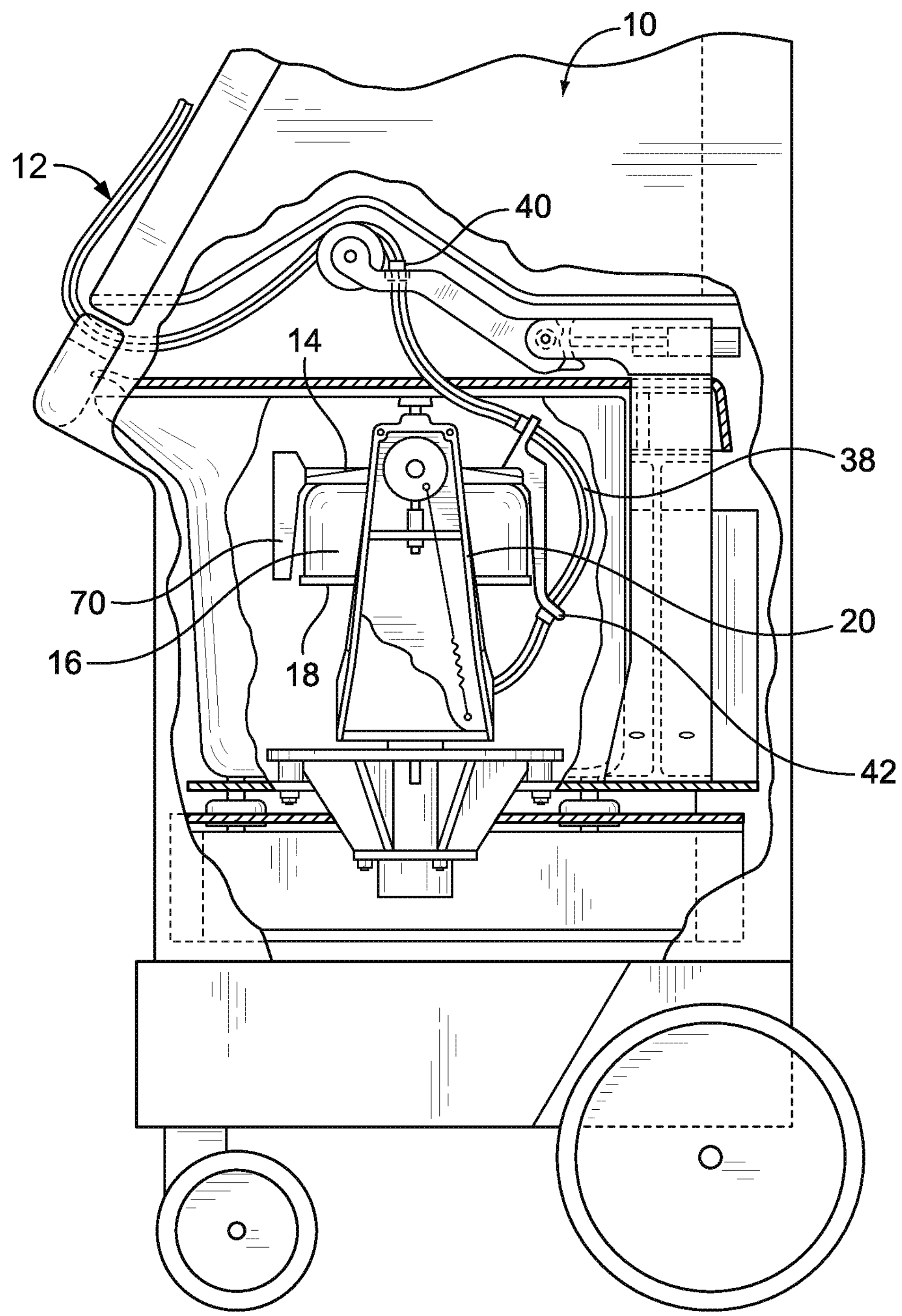
FIG. 1 is a side elevation view, with portions broken away and in section, of a centrifugal fluid separation assembly employing aspects of the present disclosure, with a centrifuge bowl and spool of the assembly being shown in their operating position.
Figure 2:
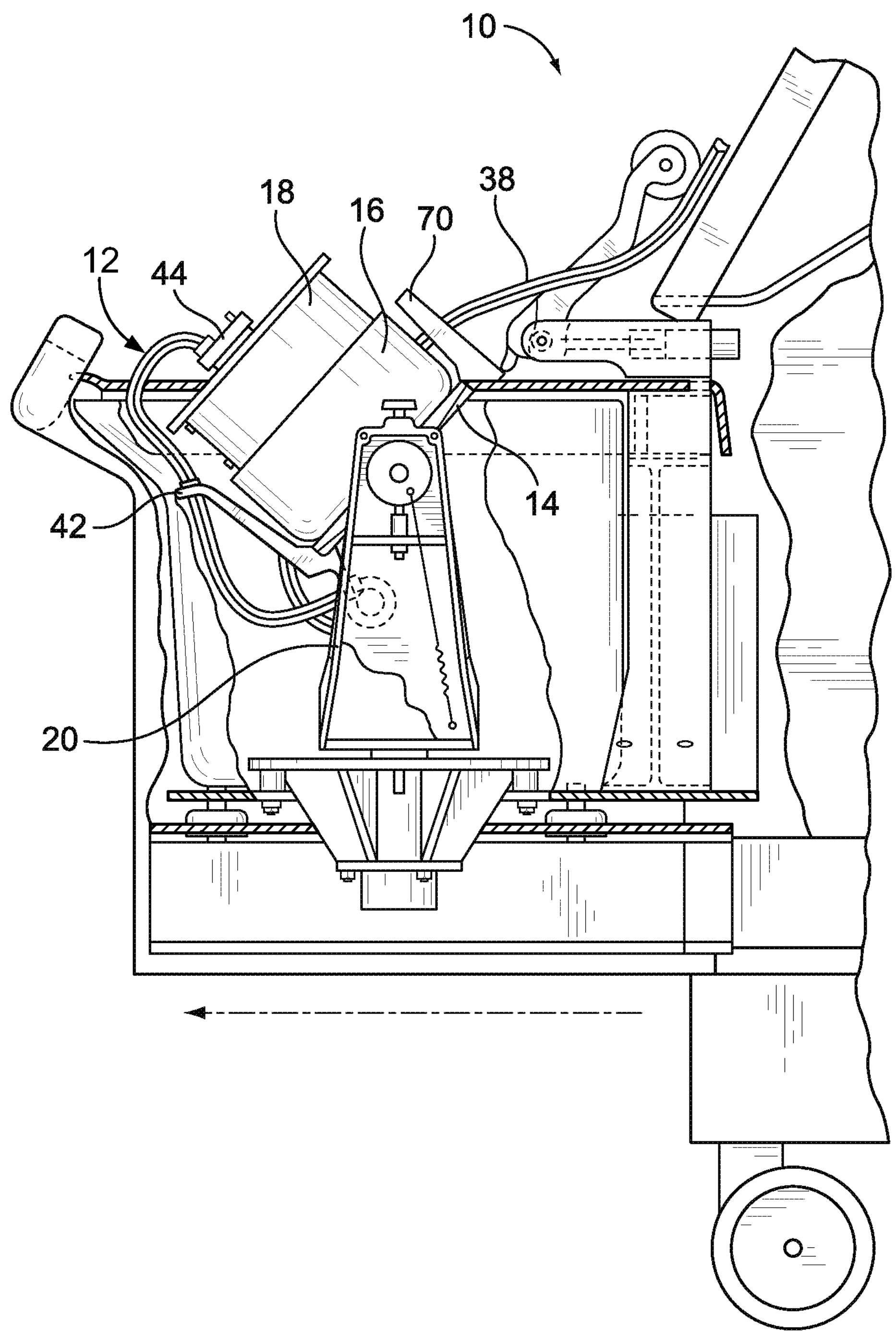
FIG. 2 is a side elevation view, with portions broken away and in section, of the assembly shown in FIG. 1, with the bowl and spool shown in an upright position for receiving a separation chamber.

FIGS. 1 and 2 show a biological fluid processing system that may be used in practicing the red blood cell and free hemoglobin differentiation principles of the present disclosure. The system is currently marketed as the AMICUS® separator of Fenwal, Inc. and is described in greater detail in U.S. Pat. No. 5,868,696. The system can be used for processing various fluids, but is particularly well suited for processing whole blood, blood components, or other suspensions of biological cellular materials. While red blood cell and free hemoglobin differentiation principles will be described herein with reference to one particular system, it should be understood that these principles may be employed with other biological fluid processing systems without departing from the scope of the present disclosure. For example, these principles may be practiced with other centrifugal separation systems (including those of the type described in greater detail in U.S. Pat. No. 7,297,272, which is hereby incorporated herein by reference), with "spinning membrane"-type separation systems (including those of the type described in greater detail in U.S. Pat. No. 9,895,482 and PCT Patent Application Publication No. WO 2017/048673 A1), and with biological fluid separation systems based on other separation principles.

A. The Centrifuge

The biological fluid processing system comprises a reusable hardware component or separation assembly 10 (FIGS. 1 and 2) and a disposable fluid flow circuit 12 (FIG. 12) that is configured to be mounted to the separation assembly 10 during use. The illustrated separation assembly 10 includes a separation device 14 (illustrated as a centrifuge) used to separate a biological fluid into two or more fluid components or constituents. The separation assembly 10 may be programmed to separate blood or a biological fluid into a variety of components (e.g., platelet-rich plasma and red blood cells), with an exemplary mononuclear cell ("MNC") collection procedure, in which the system separates and collects MNCs (e.g., lymphocytes and monocytes) from whole blood, being described herein. As noted above, it should be understood that centrifugation is only one possible separation technique that may be practiced in combination with the red blood cell and free hemoglobin differentiation principles described herein.

The illustrated centrifuge 14 is of the type shown in U.S. Pat. No. 5,316,667, which is incorporated herein by reference. The centrifuge 14 comprises a bowl 16 and a spool 18. The bowl 16 and spool 18 are pivoted on a yoke 20 between an operating position (FIG. 1) and a loading/unloading position (FIG. 2).

When in the loading/unloading position, the spool 18 can be opened by movement at least partially out of the bowl 16, as FIG. 2 shows. In this position, the operator wraps a flexible separation chamber 22 (see FIG. 3) of the fluid flow circuit 12 about the spool 18. Closure of the spool 18 and bowl 16 encloses the chamber 22 for processing. When closed, the spool 18 and bowl 16 are pivoted into the operating position of FIG. 1 for rotation about an axis.

B. The Separation Chamber

Figure 4:
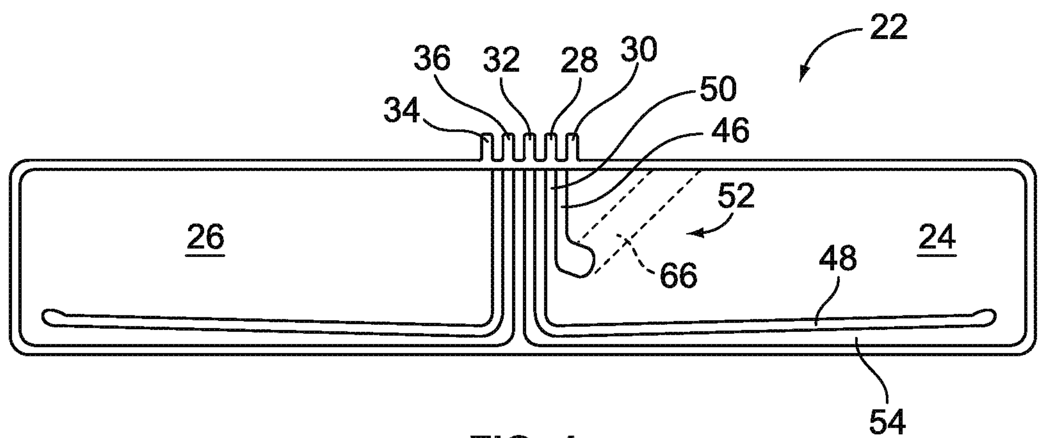
FIG. 4 is a plan view of the separation chamber shown in FIG. 3, out of association with the spool.
Figure 12:
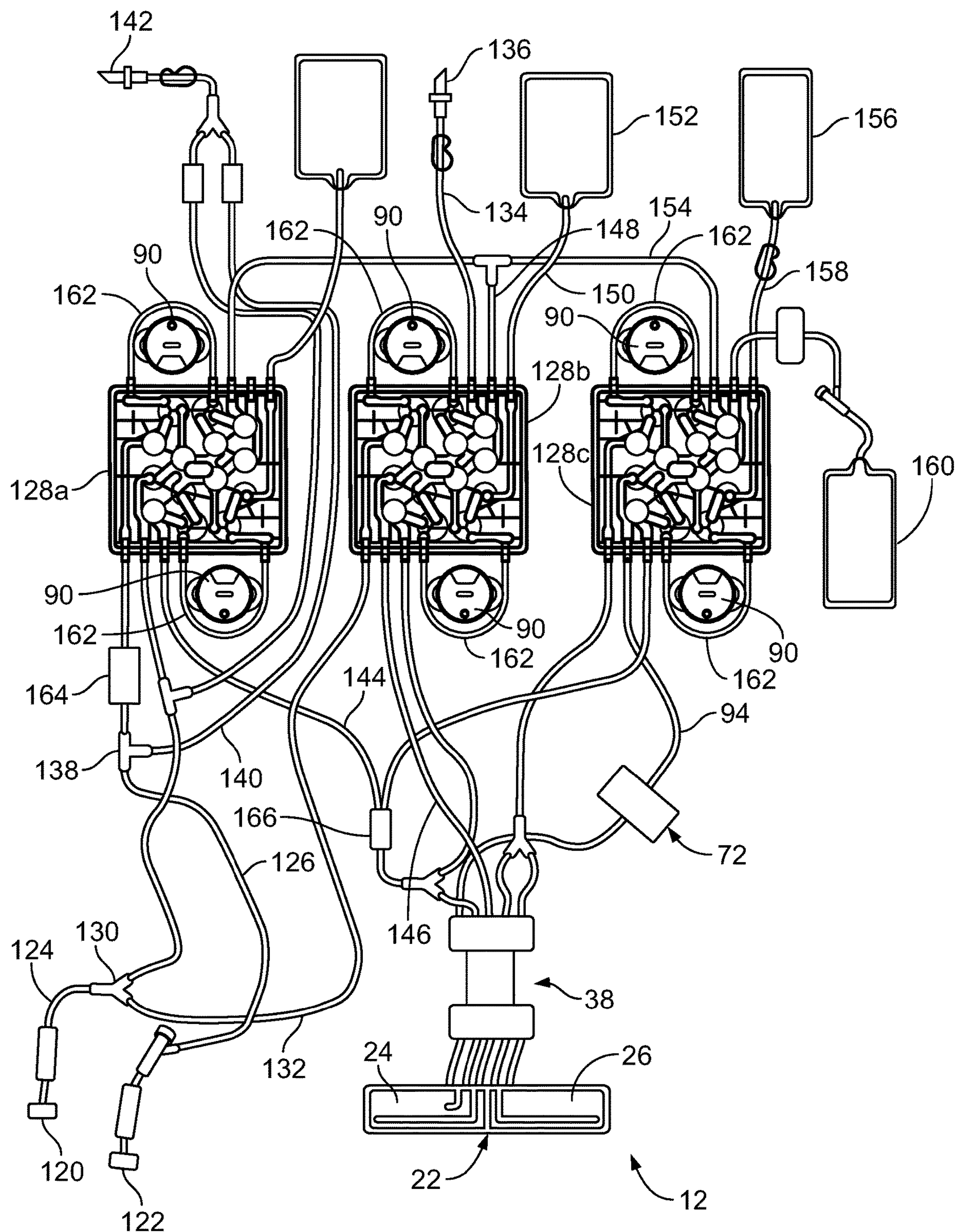
FIG. 12 is a front elevational view of an exemplary disposable fluid flow circuit that may be used in combination with the separation assembly of FIGS. 1 and 2 for carrying out biological fluid separation procedures according to the present disclosure.

The separation chamber 22 can be variously constructed. FIG. 4 shows a representative embodiment, while FIG. 12 shows the separation chamber 22 in the context of a disposable fluid flow circuit 12 that is configured for use in combination with the separation assembly 10 to define a fluid flow path for a biological fluid (e.g., blood), separated fluid components or constituents (e.g., separated blood components), and other fluids (e.g., anticoagulant). It should be understood that the red blood cell and free hemoglobin differentiation techniques described herein are not limited to monitoring of any particularly configured extracorporeal biological fluid flow circuit, but may be applied to any fluid flow circuit having an optically appropriate portion or vessel or any other optically appropriate vessel in which redness in a biological fluid changes over time.

The chamber 22 shown in FIG. 4 allows for either single- or multi-stage processing. When used for multi-stage processing, a first stage 24 separates a biological fluid (e.g., whole blood) into first and second components. Depending on the nature of the separation procedure, one of the components may be transferred into a second stage 26 for further separation. When used for single-stage processing, only the first stage 24 is used for separating a biological fluid into its constituents, while the second stage 26 may be filled with saline or the like to balance the chamber 22.

Figure 3:
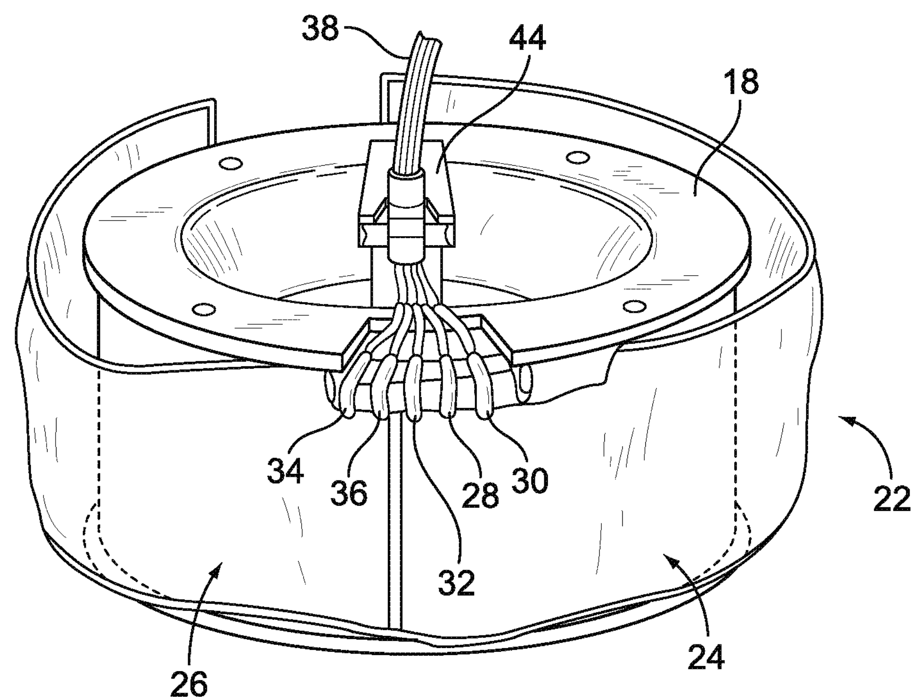
FIG. 3 is a top perspective view of the spool of the centrifuge shown in FIG. 2 in its upright position and carrying the separation chamber.

As FIGS. 3 and 4 best show, there are three ports 28, 30, and 32 associated with the first stage 24. Depending on the particular biological fluid processing procedure, the ports may have different functionality but, in an MNC collection procedure, the port identified at 28 is used for conveying fluids into the first stage 24. During such an MNC collection procedure, the other two ports 30 and 32 serve as outlet ports for separated fluid components exiting the first stage 24. More particularly, the first outlet port 30 conveys a low density fluid component from the first stage 24, while the second outlet port 32 conveys a high density fluid component from the first stage 24.

In a method of carrying out single-stage processing, at least a portion of one or more of the separated components is returned to the fluid source or to some other recipient (either of which may be a living patient or donor or a non-living source, such as a fluid container), while at least a portion of at least one of the other separated components is removed from the first stage 24 and stored. For example, a conventional MNC collection procedure (as described in greater detail in U.S. Pat. No. 5,980,760, which is hereby incorporated herein by reference) begins with a plasma collection phase. During this initial phase, whole blood in the first stage 24 is separated into a plasma constituent (i.e., a low density component, which may include platelets), an interface or buffy coat or MNC-containing layer (i.e., an intermediate density component, which includes MNCs and may also include smaller red blood cells), and packed red blood cells (i.e., a high density component). The plasma constituent and packed red blood cells are removed from the first stage 24 (via the first and second outlet ports 30 and 32, respectively), while the MNC-containing layer builds up in the first stage 24. The plasma constituent is collected, while the packed red blood cells are returned to the blood source.

When a target amount of plasma has been collected, an MNC accumulation phase begins. During this phase, the position of the interface within the first stage 24 is moved closer to the spool 18, such that platelet-rich plasma and packed red blood cells are removed from the first stage 24 (via the first and second outlet ports 30 and 32) while the MNC-containing layer continues to build up in the first stage 24. Portions of the platelet-rich plasma and the packed red blood cells are returned to the blood source, with the remainder of the platelet-rich plasma and packed red blood cells being recirculated through the first stage 24 to maintain a proper hematocrit.

When a target or preselected amount of blood has been processed, the assembly 10 transitions to a red blood cell collection phase. During this phase, blood separation continues as in the MNC accumulation phase, with recirculation and return of the platelet-rich plasma continuing, while the separated red blood cells are conveyed from the first stage 24 and collected for later use rather than being recirculated or returned to the source.

When a target amount of red blood cells have been collected, the assembly 10 transitions to an MNC harvest phase. To harvest the MNCs in the MNC-containing layer, the second outlet port 32 is closed to temporarily prevent packed red blood cells from exiting the first stage 24. At least a portion of the collected red blood cells is conveyed into the first stage 24 via the inlet port 28, which forces the MNC-containing layer to exit the first stage 24 via the first outlet port 30 for collection in an MNC collection container as an MNC product.

Following the MNC harvest phase, a plasma flush phase begins. During this phase, collected plasma is used to flush any MNC-containing layer positioned between the separation chamber 22 and the MNC collection container back into the first stage 24. A portion of the collected plasma may be conveyed into the MNC collection container as a storage or suspension medium for the MNC product.

If additional MNC product is to be collected, the various phases may be repeated. Following collection, the MNC product may be treated to further processing, such as extracorporeal photopheresis.

In a different separation procedure, in which multi-stage processing is required, one of the separated fluid components or constituents will be transferred from the first stage 24 to the second stage 26 via a port 34 associated with the second stage 26. The component transferred to the second stage 26 is further fractionated into sub-components, with one of the sub-components being removed from the second stage 26 via an outlet port 36 and the other sub-component remaining in the second stage 26.

As best shown in FIG. 3, a tubing umbilicus 38 is attached to the ports 28, 30, 32, 34, and 36. The umbilicus 38 interconnects the first and second stages 24 and 26 with each other and with pumps and other stationary components located outside the rotating components of the centrifuge 14 (not shown). As FIG. 1 shows, a non-rotating (zero omega) holder 40 holds the upper portion of the umbilicus 38 in a non-rotating position above the spool 18 and bowl 16. A holder 42 on the yoke 20 rotates the mid-portion of the umbilicus 38 at a first (one omega) speed about the suspended spool 18 and bowl 16. Another holder 44 (FIGS. 2 and 3) rotates the lower end of the umbilicus 38 at a second speed twice the one omega speed (the two omega speed), at which speed the spool 18 and bowl 16 also rotate. This known relative rotation of the umbilicus 38 keeps it untwisted, in this way avoiding the need for rotating seals.

As FIG. 4 shows, a first interior seal 46 is located between the low density outlet port 30 and the inlet port 28. A second interior seal 48 is located between the inlet port 28 and the high density outlet port 32. The interior seals 46 and 48 form a fluid passage 50 (an inlet for whole blood or the like) and a low density collection region 52 in the first stage 24. The second seal 48 also forms a fluid passage 54 (a high density blood component outlet in an MNC collection procedure) in the first stage 24.

Figure 5:
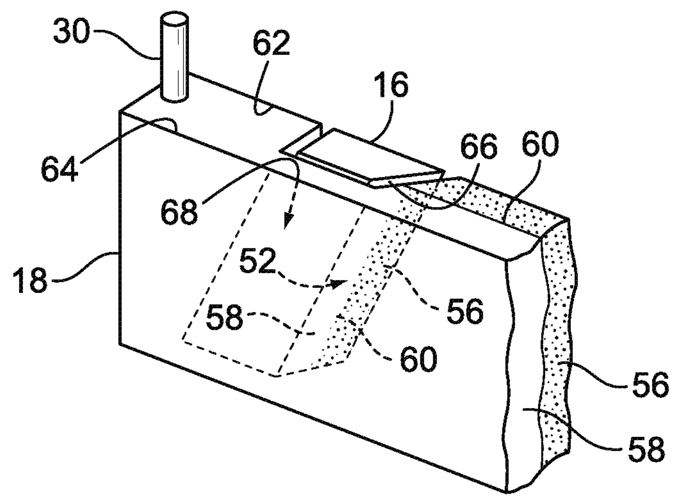
FIG. 5 is an enlarged perspective view of an interface ramp carried by the centrifuge in association with the separation chamber, showing the centrifugally separated red blood cell layer, plasma layer, and interface within the separation chamber when in a desired location on the ramp.

In an MNC collection procedure, the fluid passage 50 channels blood directly into the circumferential flow path immediately next to the low density collection region 52. As shown in FIG. 5, the blood separates into an optically dense layer 56 containing cellular components, which forms as cellular components move under the influence of centrifugal force toward the high-G (outer) wall 62. The optically dense layer 56 will include red blood cells (and, hence, will be referred to herein as the "RBC layer") but, depending on the speed at which the centrifuge 14 is spun, other cellular components (e.g., larger white blood cells and platelets) may also be present in the RBC layer 56.

The movement of the component(s) of the RBC layer 56 displaces less dense blood components radially toward the low-G (inner) wall 64, forming a second, less optically dense layer 58. The less optically dense layer 58 includes plasma (and, hence, will be referred to herein as the "plasma layer or plasma constituent") but, depending on the speed at which the centrifuge 14 is rotated and the length of time that the blood is resident in the centrifuge, other components (e.g., smaller platelets) may also be present in the plasma layer 58.

The transition between the RBC layer 56 and the plasma layer 58 is generally referred to as the interface or buffy coat or MNC-containing layer 60, as described above and shown in FIG. 5. Platelets and white blood cells (including MNCs) typically occupy this transition region.

Figure 6:
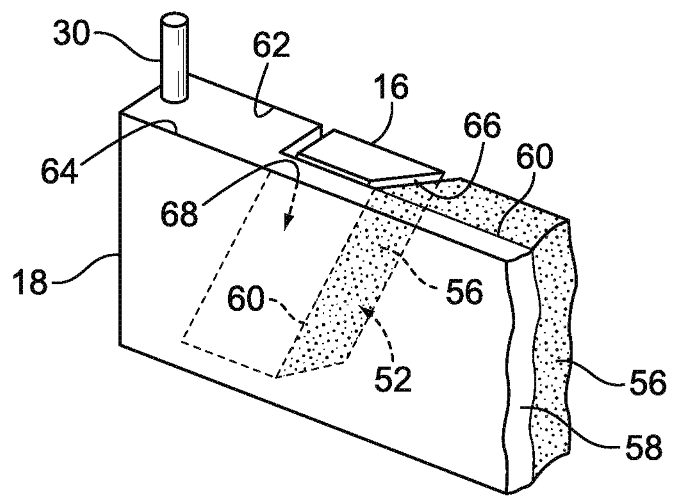
FIG. 6 is an enlarged perspective view of the interface ramp shown in FIG. 5, showing the red blood cell layer and interface at an undesired high location on the ramp.
Figure 7:
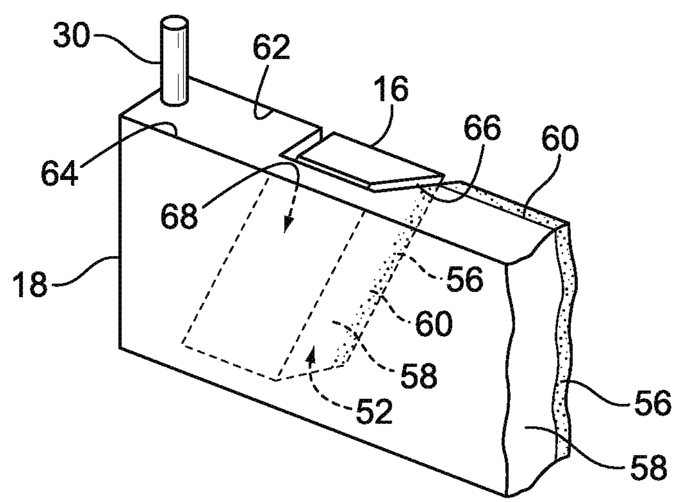
FIG. 7 is an enlarged perspective view of the interface ramp shown in FIG. 5, showing the red blood cell layer and interface at an undesired low location on the ramp.

The location of the interface 60 within the chamber 22 can dynamically shift during blood processing, as FIGS. 6 and 7 show. If the location of the interface 60 is too high (that is, if it is too close to the low-G wall 64 and the removal port 30, as FIG. 6 shows), red blood cells can spill over and into the low density collection region 52, adversely affecting the quality of the plasma constituent 58. On the other hand, if the location of the interface 60 is too low (that is, if it resides too far away from the low-G wall 64, as FIG. 7 shows), the collection efficiency of the assembly 10 may be impaired.

As FIG. 5 shows, a ramp 66 extends from the high-G wall 62 of the bowl 16 at an angle across the low density collection region 52. The angle, measured with respect to the axis of the first outlet port 30 is about 30° in one embodiment. FIG. 5 shows the orientation of the ramp 66 when viewed from the low-G wall 64 of the spool 18. FIG. 4 shows, in phantom lines, the orientation of the ramp 66 when viewed from the high-G wall 62 of the bowl 16.

Further details of the angled relationship of the ramp 66 and the first outlet port 30 can be found in U.S. Pat. No. 5,632,893, which is incorporated herein by reference.

The ramp 66 forms a tapered wedge that restricts the flow of fluid toward the first outlet port 30. The top edge of the ramp 66 extends to form a constricted passage 68 along the low-G wall 64. The plasma layer 58 must flow through the constricted passage 68 to reach the first outlet port 30.

As FIG. 5 shows, the ramp 66 makes the interface 60 between the RBC layer 56 and the plasma layer 58 more discernible for detection, displaying the RBC layer 56, plasma layer 58, and interface 60 for viewing through the high-G wall 62 of the chamber 22.

Further details of the separation chamber 22 and its operation may be found in U.S. Pat. No. 5,316,667.

C. The Interface Controller

An interface controller (FIG. 11) includes a viewing head or interface optical sensor device 70 carried on the yoke 20 (see FIGS. 1 and 8) and a differentiating optical sensor device 72, which is shown as being associated with tubing connected to the first outlet port 30 (but which may be variously positioned, as will be described in greater detail herein). Alternatively, rather than being carried on the yoke 20, the interface optical sensor device 70 may be mounted to a radial location of the centrifuge bucket or enclosure, as described in U.S. Patent Application Publication Nos. 2014/0057771 and 2015/0219558, both of which are incorporated herein by reference. The interface optical sensor device 70 is oriented to optically view the transition in optical density between the RBC layer 56 and the plasma layer 58 on the ramp 66. The differentiating optical sensor device 72 determines whether redness in fluid in an associated portion or vessel of the fluid flow circuit 12 (fluid flowing out of the first stage 24 via the first outlet port 30 in the illustrated embodiment) is due to the presence of red blood cells or free hemoglobin, as will be described in greater detail herein.

The interface controller is functional to determine the location of the interface 60 on the ramp 66 and, if the interface 60 is located at an improper location (e.g., in the locations of FIG. 6 or 7), to correct the location of the interface 60.

(1) The Interface Optical Sensor Device

Figure 8:
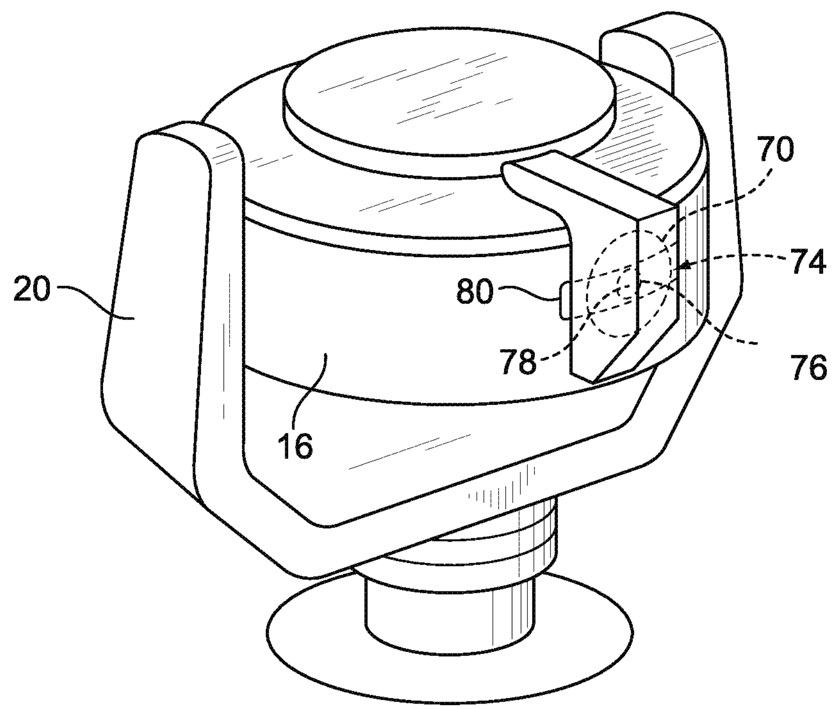
FIG. 8 is a side perspective view of the bowl and spool of the centrifuge when in the operating position, showing a viewing head, which forms a part of an interface controller, being carried by the centrifuge to view the interface ramp during rotation of the bowl.
Figure 9:
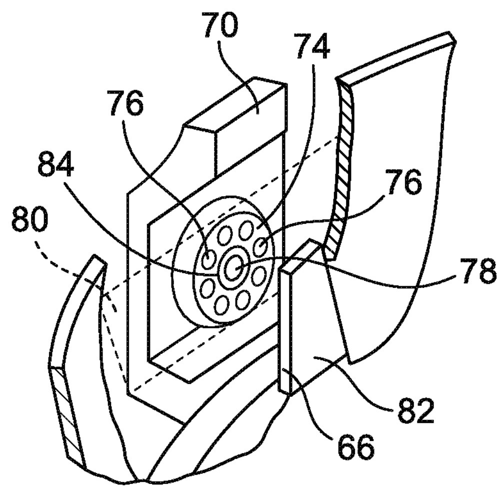
FIG. 9 is a perspective view of the viewing head, with portions broken away and in section, showing the light source and light detector, which are carried by the viewing head, in alignment with the interface ramp, as viewed from within the spool and bowl of the centrifuge.
Figure 10:
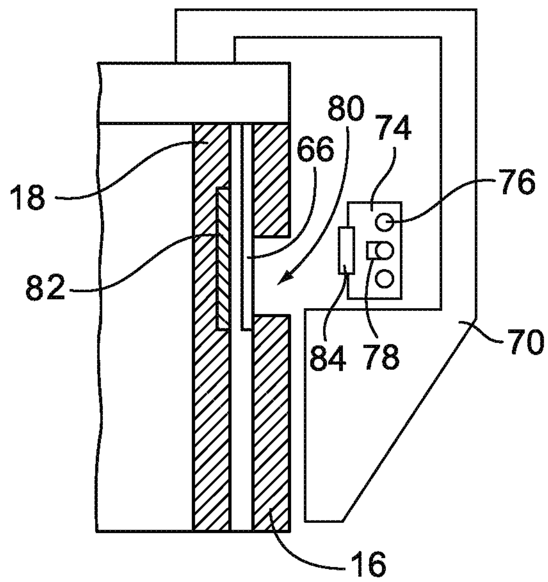
FIG. 10 is a side section view of the bowl, spool, and viewing head when the viewing head is aligned with the interface ramp.

Referring to FIGS. 8-10, the interface optical sensor device 70, carried by the yoke 20 or mounted to a stationary radial location of the centrifuge bucket or enclosure, includes a light source 74, which emits light that is scattered and absorbed by red blood cells. In the illustrated embodiment, the light source 74 includes a circular array of red light emitting diodes 76, but other wavelengths scattered or absorbed by red blood cells, like green or infrared, could also be used.

In the illustrated embodiment, seven light emitting diodes 76 comprise the light source 74. More diodes 76 may be used, or fewer diodes 76 can be used, depending upon the optical characteristics desired. Further, non-LED lights may also be employed without departing from the scope of the present disclosure.

The interface optical sensor device 70 also includes a light detector 78 (FIGS. 9 and 10), which is mounted adjacent to the light source 74. In one embodiment, the light detector 78 comprises a PIN diode detector, which is located generally in the geometric center of the circular array of light emitting diodes 76. Other types of light detectors may also be employed.

If mounted to the yoke 20, the yoke 20 and the interface optical sensor device 70 rotate at a one omega speed, as the spool 18 and bowl 16 rotate at an average speed of two omega. If mounted to a stationary portion of the centrifuge bucket or enclosure, the interface optical sensor device 70 remains stationary while the yoke 20 rotates at a one omega speed and the spool 18 and bowl 16 rotate at an average speed of two omega. The light source 74 directs light onto the rotating bowl 16. In the illustrated embodiment, the bowl 16 is transparent to the light emitted by the source 74 only in the region 80 where the bowl 16 overlies the interface ramp 66 (FIG. 8). In the illustrated embodiment, the region 80 comprises a window cut out in the bowl 16. The remainder of the bowl 16 that lies in the path of the interface optical sensor device 70 comprises an opaque or light absorbing material.

The interface ramp 66 is made of a light transmissive material. The light from the source 74 will thereby pass through the transparent region 80 of the bowl 16 and the ramp 66 every time the rotating bowl 16 and interface optical sensor device 70 align. The spool 18 may also carry a light reflective material 82 (FIGS. 9 and 10) behind the interface ramp 66 to enhance its reflective properties. The spool 18 reflects incoming light received from the source 74 out through the transparent region 80 of the bowl 16, where it is sensed by the detector 78. In the illustrated embodiment, light passing outward from the source 74 and inward toward the detector 78 passes through a focusing lens 84 (shown in FIGS. 9 and 10), which forms a part of the viewing head 70.

Such an arrangement optically differentiates the reflective properties of the interface ramp 66 from the remainder of the bowl 16. This objective can be achieved in other ways. For example, the light source 74 could be gated on and off with the arrival and passage of the ramp 66 relative to its line of sight. As another example, the bowl 16 outside the transparent region 80 could carry a material that reflects light, but at a different intensity than the reflective material 82 behind the interface ramp 66.

As the transparent interface region 80 of the bowl 16 comes into alignment with the interface optical sensor device 70, the detector 78 will first sense light reflected through the plasma layer 58 on the ramp 66. Eventually, the RBC layer 56 adjacent the interface 60 on the ramp 66 will enter the optical path of the interface optical sensor device 70. The RBC layer 56 scatters and absorbs light from the source 74 and thereby reduces the previously sensed intensity of the reflected light. The length of time that the higher intensity of reflected light is sensed by the detector 78 represents the amount of light from the source 74 that is not scattered or absorbed by the RBC layer 56 adjacent to the interface 60. With this information, a processing element or module 86 (FIG. 11) can determine the location of the interface 60 on the ramp 66 relative to the constricted passage 68. A more detailed discussion of the algorithms by which the interface controller receives and processes signals to determine the location of the interface 60 on the ramp 66 may be found in U.S. Pat. No. 6,312,607, which is incorporated herein by reference.

Figure 11:
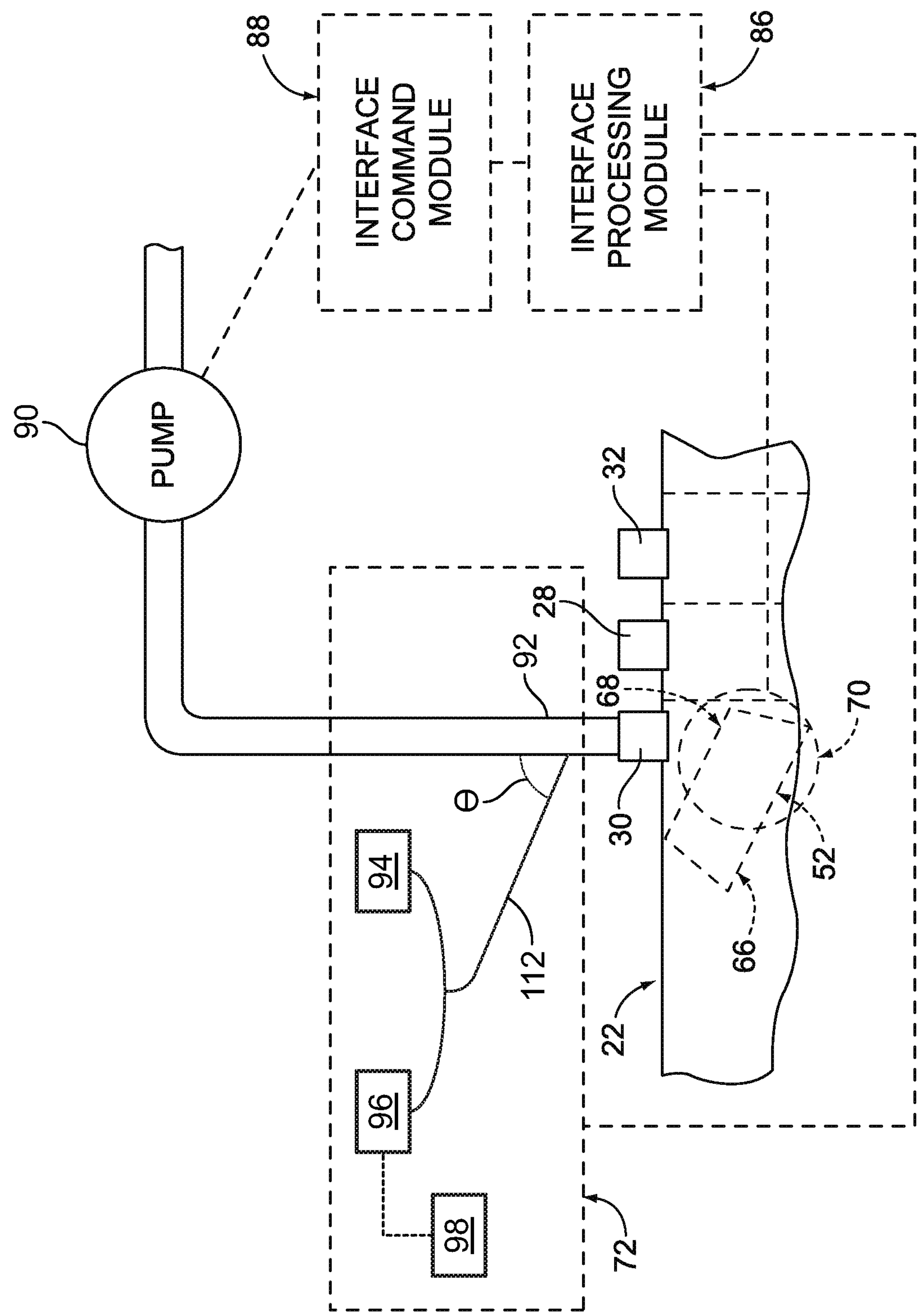
FIG. 11 is a schematic view of components of the interface controller including a differentiating optical sensor device.

When the location of the interface 60 on the ramp 66 has been determined, the processing element 86 outputs that information to an interface command element or module 88 (FIG. 11). The command element 88 includes a comparator, which compares the interface location output with a desired interface location to generate an error signal. The error signal may take a number of forms but, in one embodiment, is expressed in terms of a targeted red blood cell percentage value (i.e., the percentage of the ramp 66 which should be occupied by the RBC layer 56).

When the control value is expressed in terms of a targeted red blood cell percentage value, a positive error signal indicates that the RBC layer 56 on the ramp 66 is too small (as FIG. 7 shows). The interface command element 88 generates a signal to adjust an operational parameter accordingly, such as by increasing the rate at which plasma is removed through the first outlet port 30 under action of a pump 90 (FIG. 11). The interface 60 moves toward the constricted passage 68 to the desired control position (as FIG. 5 shows), where the error signal is zero.

A negative error signal indicates that the RBC layer 56 on the ramp 66 is too large (as FIG. 6 shows). The interface command element 88 generates a signal to adjust an operational parameter accordingly, such as by decreasing the rate at which plasma is removed through the first outlet port 30. The interface 60 moves away from the constricted passage 68 to the desired control position (FIG. 5), where the error signal is again zero.

(2) The Differentiating Optical Sensor Device

The interface controller may further include a differentiating optical sensor device 72 (FIG. 11), which is shown as being configured to monitor the fluid exiting the first stage 24 of the separation chamber 22 via the first outlet port 30. The fluid exiting the first stage 24 via the first outlet port 30 is typically platelet-poor plasma or platelet-rich plasma, but depends on the procedure being executed by the system. For example, the MNC-containing layer will and the RBC layer may exit the first outlet port 30 during the MNC harvest phase of an MNC collection procedure of the type described herein.

While the differentiating optical sensor device 72 is shown as monitoring a tube 92 connected to the first outlet port 30, it should be understood that the differentiating optical sensor device 72 may be located and configured to monitor fluid in any optically appropriate portion or vessel of the fluid flow circuit 12 in which redness in the fluid is subject to change. This may include vessels in which fluid is in motion (e.g., flowing through a tube or through the separation chamber 22 or a cassette) and vessels in which fluid is substantially stationary (e.g., a collection or storage bag or container), as well as vessels positioned either upstream or downstream of the separation chamber 22. Furthermore, while the illustrated differentiating optical sensor device 72 is shown as being incorporated into the interface controller, it is also within the scope of the present disclosure for the differentiating optical sensor device 72 to be separately provided and either work cooperatively with the interface controller or entirely independently.

The differentiating optical sensor device 72 compares the intensity of a wavelength of light reflected by the fluid in the associated vessel at two different times to assess whether redness in the fluid is due to the presence of red blood cells or free hemoglobin. For fluid flowing through the tube 92 connected to the first outlet port 30, the redness in the fluid will typically increase over time, due to an increasing amount of red blood cells or free hemoglobin in the fluid. In this case, an increase in the intensity of the wavelength of the reflected light is indicative of the presence of red blood cells, whereas a decrease in the intensity of the wavelength of the reflected light is indicative of the presence of free hemoglobin. However, in other settings, the redness in a monitored fluid may decrease over time, in which case, an increase in the intensity of the wavelength of the reflected light is indicative of the presence of free hemoglobin, while a decrease in the intensity of the wavelength of the reflected light is indicative of the presence of red blood cells.

The information obtained and output by the differentiating optical sensor device 72 may be used to modify the separation procedure, such as by changing the speed at which a pump 90 operates or causing the transition from one phase of a separation procedure to another phase. For example, if the output is indicative of the presence of red blood cells in a subject fluid that is intended to be substantially free of red blood cells, the output may be used modify the separation procedure in a way that reduces contamination of the fluid by red blood cells (e.g., by moving the position of the interface 60 within the separation chamber 22). If the output is indicative of an elevated free hemoglobin concentration, the output may be used to modify the separation procedure in a way that reduces the incidence of hemolysis (e.g., by reducing the rate at which the separation device is rotated).

The differentiating optical sensor device 72 includes a light source 94, a light detector 96, and a controller 98. The light source is configured to emit a light including a wavelength in a range of 650 nm to 900 nm, which is the range over which varying hematocrit and free hemoglobin concentration levels lead to varying light reflection intensity, as will be described in greater detail herein. This may include a single wavelength light source (i.e., a light source configured to emit light having a single wavelength in the range of 650 nm to 900 nm, which may be 810 nm in one embodiment) or a broadband light source (i.e., a light source configured to emit light having a plurality of wavelengths, including at least one wavelength in the range of 650 nm to 900 nm). If provided as a broadband light source, the light source 94 may be configured to emit a light including at least all wavelengths in the visible range (from approximately 400 nm to approximately 700 nm), but may also emit light including wavelengths above and/or below the visible range. In one embodiment, the light source 94 is provided as a stabilized tungsten-halogen light source (configured to emit a light having all wavelengths between 360 nm and 2600 nm) of the type marketed by Thorlabs, Inc. of Newton, N.J., but the light source 94 may also be differently configured without departing from the scope of the present disclosure.

Figure 13:
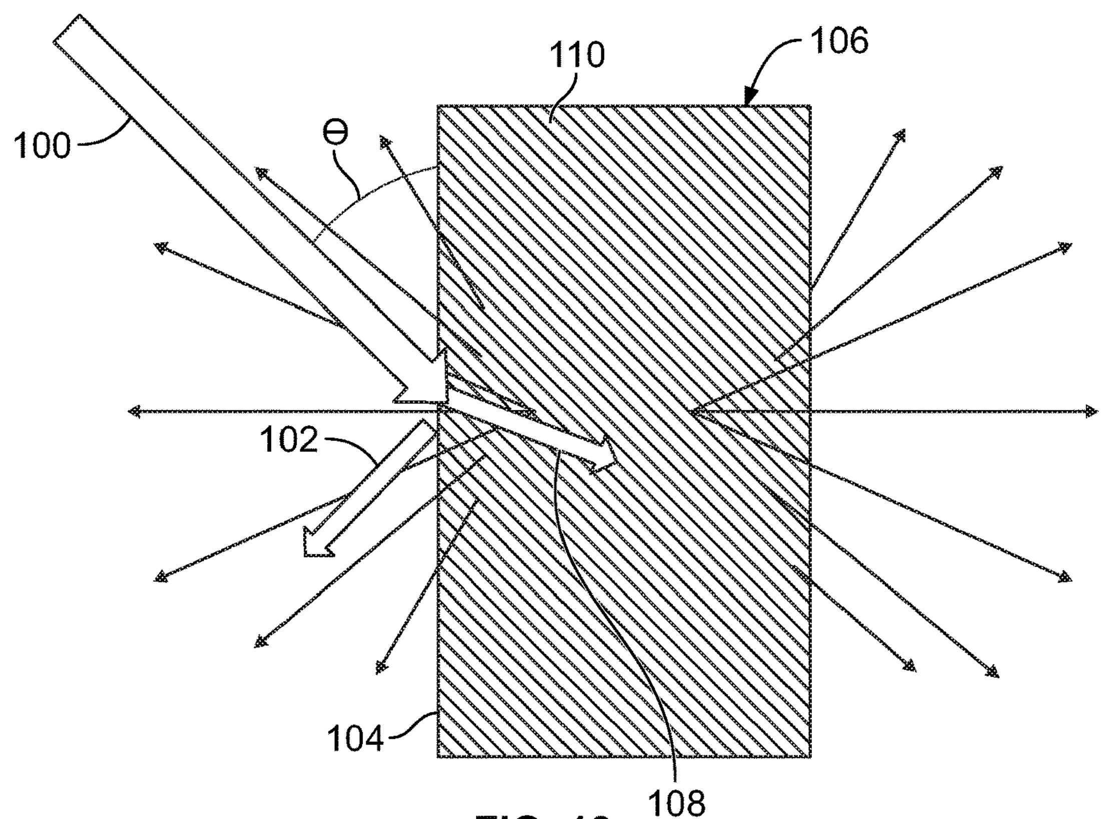
FIG. 13 is a schematic view of light from a light source of the differentiating optical sensor device of FIG. 11 entering into a fluid-containing vessel.

The light source 94 is oriented to emit light toward a vessel of the fluid flow circuit 12 (the tube 92 in FIG. 11) in which fluid is present. FIG. 13 shows the light 100 emitted by the light source 94, with a first portion 102 of the light 100 reflecting off of a surface 104 of the vessel 106 (specular reflection), while a second portion 108 of the light 100 is transmitted through the surface 104 and into the vessel 106. As shown in FIGS. 11 and 13, the light 100 may be directed to strike the surface 104 of the vessel 106 at an angle ⊖, which may be selected to reduce the degree of specular reflection. For example, if the angle ⊖ is 90°, there will tend to be a significant amount of specular reflection. On the other hand, if the angle ⊖ is 0° (i.e., if the light 100 is parallel to the surface 104), then the fluid 110 in the vessel 106 will not be exposed to any light. It has been found that an angle in the range of 30-60° (which may be approximately 45°, in one embodiment) may be advantageous for reducing the degree of specular reflection and producing more sensitive color measurements.

Figure 14:
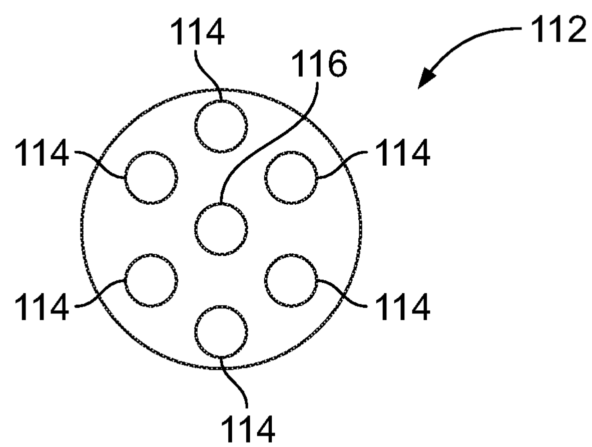
FIG. 14 is a cross-sectional view of an optical bundle of the differentiating optical sensor device of FIG. 11.

The light source 94 itself may be oriented to direct the light 100 at a particular angle ⊖ with respect to the surface 104 of the vessel 106. Alternatively, at least one transmitting optical fiber may be provided to direct at least a portion of the light 100 from the light source 94 to the surface 104 of the vessel 106 at a particular angle ⊖. FIG. 11 shows an optical fiber bundle 112, which includes a plurality of optical fibers. In one embodiment, the optical fiber bundle 112 is provided as a fiber bundle reflection probe of the type marketed by Thorlabs, Inc., having optical fibers with a 200 μm diameter. A cross-sectional view of the optical fiber bundle 112 is shown in FIG. 14, which shows seven optical fibers, with six outer optical fibers 114 and one inner optical fiber 116 positioned centrally with respect to the other optical fibers 114. In the illustrated embodiment, the outer optical fibers 114 comprise transmitting optical fibers configured to transmit light from the light source 94 to the surface 104 of the vessel 106, while the central or inner optical fiber 116 comprises a receiving optical fiber configured to transmit reflected light to the light detector 96. It should be understood that the illustrated configuration of the optical fiber bundle 112 is merely exemplary and that other configurations may also be employed if an optical fiber bundle is provided. For example, in other embodiments, there may be only a single transmitting optical fiber, a plurality of receiving optical fibers, and/or optical fibers differently arranged than as shown in FIG. 14.

Figure 15:
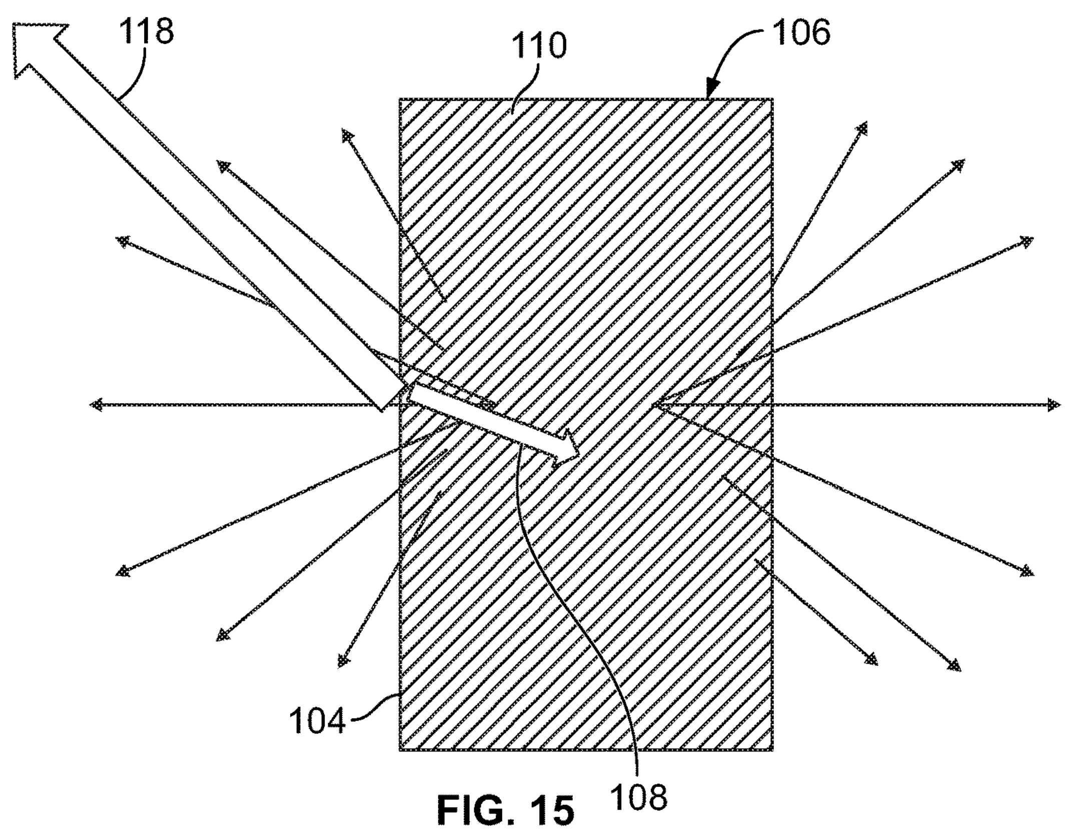
FIG. 15 is a schematic view of light reflecting off of the fluid in the vessel of FIG. 13 for receipt and analysis by the differentiating optical sensor device of FIG. 11.

The light 100 strikes the surface 104 of the vessel 106 and the portion 108 not reflected is transmitted through the surface 104 and into the vessel 106 at an angle according to Snell's Law. The portion 108 of light that enters the fluid 110 is absorbed and scattered based on the unique optical properties of the fluid 110, with a portion 118 of the transmitted light 108 being reflected back out of the vessel 106 (FIG. 15) for receipt by the light detector 96. If a receiving optical fiber 116 is provided, at least a portion of the reflected light 118 is directed to the light detector 96 by the receiving optical fiber 116.

The light detector 96 is configured for measurement of the intensity of the target wavelength of at least a portion of the reflected light that it receives at first and second times. If the reflected light includes a plurality of wavelengths, the light detector 96 may be provided as an optical spectrometer, which is further configured for wavelength differentiation to isolate the target wavelength and measure its intensity. In one embodiment, the light detector 96 is provided as a compact CCD spectrometer capable of measuring the intensity of light at each wavelength in the range of 200 nm-1000 nm of the type marketed by Thorlabs, Inc., but it may also be differently configured without departing from the scope of the present disclosure.

At the first time, which may be the time at which the subject fluid is first exposed to the light from the light source 94, the light detector 96 measures the intensity of the target wavelength of at least a portion of the reflected light that it receives. The degree of redness in the fluid is also noted. The manner in which redness is assessed may vary without departing from the scope of the present disclosure. For example, in one embodiment, the differentiating optical sensor device 72 may be provided as a colorimetric optical sensor device, which is capable of measuring the degree of redness in a subject fluid. A suitable colorimetric optical sensor device is described in greater detail in U.S. Provisional Patent Application Ser. No. 62/657,397, filed on Apr. 13, 2018, which is hereby incorporated herein by reference. If the differentiating optical sensor device 72 is itself capable of assessing the degree of redness in the subject fluid, it may do so, with the controller 98 saving that information as the degree of redness in the fluid at the first time.

On the other hand, if the differentiating optical sensor device 72 is not itself configured to determine the degree of redness in the subject fluid, then a separate "redness" optical sensor device may be provided to monitor the same fluid being monitored by the differentiating optical sensor device 72. Such a separate optical sensor device may be variously configured without departing from the scope of the present disclosure. For example, such a separate optical sensor device may be configured according to the description of the optical sensing station in U.S. Pat. No. 7,011,761, which is hereby incorporated herein by reference. When this separate optical sensor device has determined the degree of redness in the fluid, it may generate an output that is received by the controller 98 of the differentiating optical sensor device 72 as the degree of redness in the fluid at the first time. The "redness" optical sensor device later assesses the redness in the fluid again (which may be at the same "second time" at which the differentiating optical sensor device 72 is measuring the intensity of the target wavelength of at least a portion of the reflected light that it is receiving) and may generate a second output that is received by the controller 98 of the differentiating optical sensor device 72 as the degree of redness in the fluid at the second time. The controller 98 of the differentiating optical sensor device 72 compares the two outputs from the "redness" optical sensor device to determine whether redness in the fluid has increased or decreased from the first time to the second time. Alternatively, rather than the "redness" optical sensor device providing the differentiating optical sensor device 72 with two outputs, the "redness" optical sensor device may record and compare the degree of redness in the fluid at the first and second times and then generate a single output that is received by the controller 98 of the differentiating optical sensor device 72, which single output informs the controller 98 that the redness in the fluid has increased or decreased from the first time to the second time.

In yet another embodiment, if the differentiating optical sensor device 72 is not configured to assess fluid redness and if an associated "redness" optical sensor device is not provided, then an operator may visually assess the degree of redness in the fluid and notify the separation assembly 10 that the redness in the fluid has increased or decreased from the first time to the second time.

As alluded to, at a second time that is subsequent to the first time, the light detector 96 measures the intensity of the target wavelength of at least a portion of the reflected light that it receives. The degree of redness in the fluid is again noted according to any suitable approach (e.g., by the differentiating optical sensor device 72 itself measuring the degree of redness, by a separate "redness" optical sensor device, or by an operator).

With these pieces of information, the controller 98 of the differentiating optical sensor device 72 determines whether the intensity of the target wavelength of at least a portion of the reflected light that the light detector 96 received at the first and second times has increased or decreased from the first time to the second time and whether the redness in the subject fluid has increased or decreased from the first time to the second time. The controller 98 may be variously configured without departing from the scope of the present disclosure. In one embodiment, the controller 98 may include a microprocessor (which, in fact may include multiple physical and/or virtual processors). According to other embodiments, the controller 98 may include one or more electrical circuits designed to carry out the actions described herein. In fact, the controller 98 may include a microprocessor and other circuits or circuitry. In addition, the controller 98 may include one or more memories. The instructions by which the microprocessor is programmed may be stored on the memory associated with the microprocessor, which memory/memories may include one or more tangible non-transitory computer readable memories, having computer executable instructions stored thereon, which when executed by the microprocessor, may cause the microprocessor to carry out one or more actions as described below.

Knowing whether the intensity of the target wavelength and the degree of redness in the subject fluid have increased or decreased from the first time to the second time allows the controller 98 to determine whether the redness in the fluid is due to the presence of red blood cells or free hemoglobin due to a difference in the degree of light reflected upon increasing hematocrit versus the degree of light reflected upon increasing free hemoglobin concentration.

Figure 16:
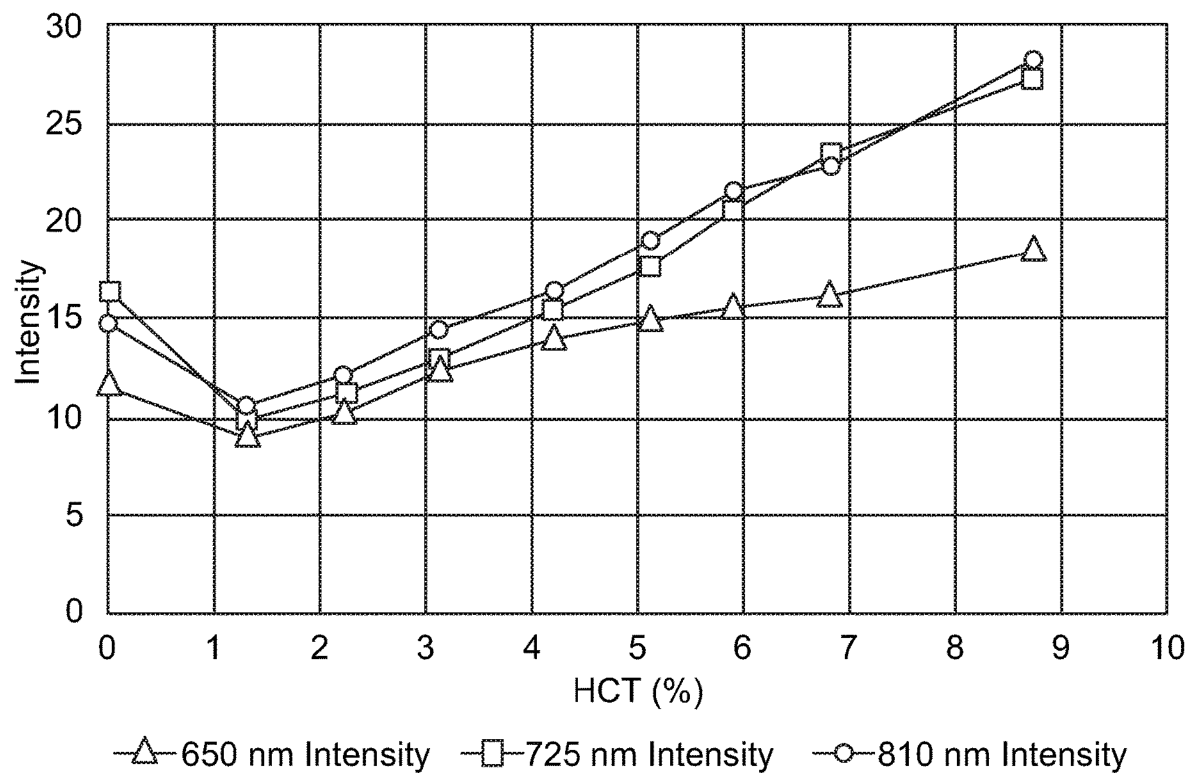
FIG. 16 is a chart illustrating a relationship between hematocrit and the intensity of reflected light for different wavelengths of light reflected by a fluid.

In particular, in accordance with the methods and sensors described herein, as a fluid becomes darker red, if the cause of the redness is the presence of red blood cells, the intensity or amount of reflected light will increase. This relationship between hematocrit and intensity or amount of reflected light can be seen in FIG. 16, which compares hematocrit at wavelengths of 650 nm, 725 nm, and 810 nm to the intensity of reflected light. As can be seen, above 1% hematocrit, the intensity of reflected light increases with increasing hematocrit. However, the intensity of reflected light actually decreases from 0% to 1% hematocrit, which could lead to misleading results. Accordingly, in view of this initial decrease in intensity from 0% to 1% hematocrit, it may be preferred for the principles described herein to be limited to fluid having a hematocrit greater than 1%. This is not considered to be a significant limitation because, when red blood cells leak out of a centrifuge or other separation device, hematocrit tends to increase until corrective action is taken, with 1% hematocrit typically being reached relatively quickly. Thus, a hematocrit of less than 1% in such a typical leakage scenario is rare.

Figure 17:
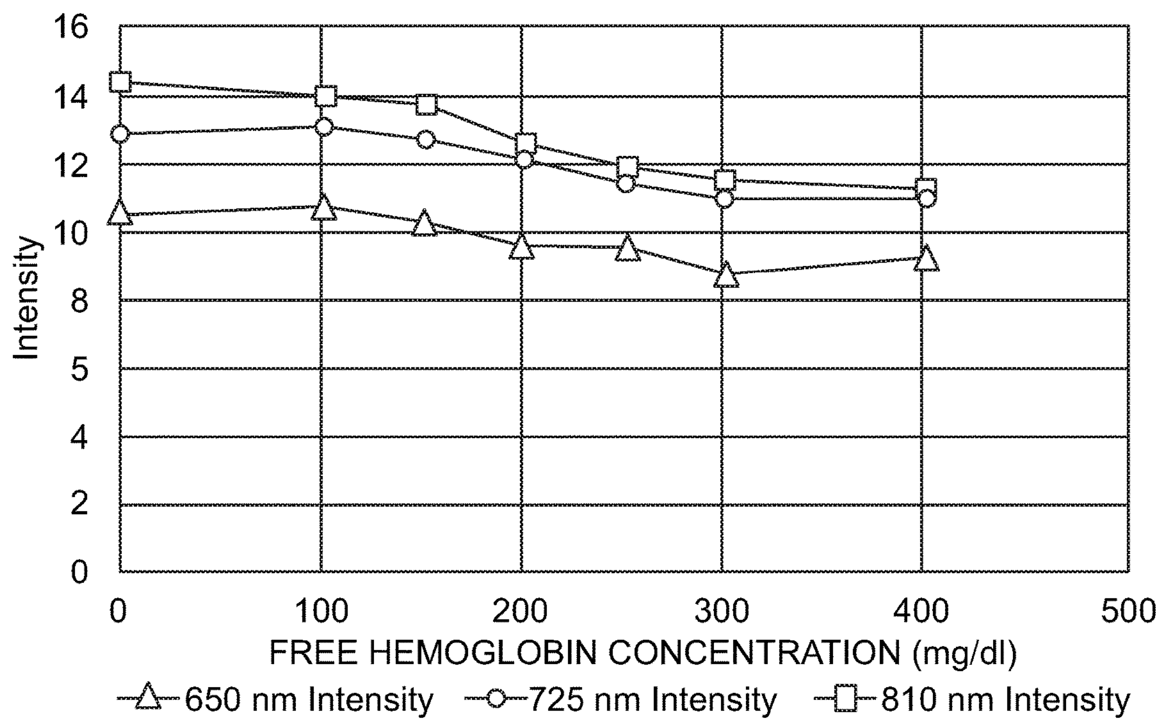
FIG. 17 is a chart illustrating a relationship between free hemoglobin concentration and the intensity of reflected light for different wavelengths of light reflected by a fluid.

On the other hand, in accordance with the methods and sensors described herein, as a fluid becomes darker red, if the cause of the redness is the presence of free hemoglobin, the intensity or amount of reflected light will decrease. This relationship between free hemoglobin concentration and intensity or amount of reflected light can be seen in FIG. 17, which compares free hemoglobin concentration (in mg/dL) at wavelengths of 650 nm, 725 nm, and 810 nm to the intensity of reflected light. As can be seen, the intensity of reflected light remains constant or decreases with increasing free hemoglobin concentration, in contrast to the intensity of reflected light increasing with increasing hematocrit over 1%.

This phenomenon is believed to be attributed to the light absorption that occurs with free hemoglobin in contrast to the significant scattering that is introduced once red blood cells (which are much larger than the wavelength of the incident light) are present in the subject fluid. When light is directed into a fluid, such as substantially cell-free plasma, a majority of the light is transmitted through the fluid, with very small amounts of light being absorbed or scattered by particles present in the fluid. As the concentration of free hemoglobin particles begins to increase, more light is absorbed by the hemoglobin than scattered (as hemoglobin is the primary light absorber in blood), with light previously reflected back to the light detector 96 being instead absorbed, leading to the decrease in light intensity upon increasing free hemoglobin concentration illustrated in FIG. 17. Plasma with free hemoglobin may, thus, be considered an absorption media, as the extinction of light traveling through it is accomplished more so by absorption than by scattering. On the other hand, as red blood cell concentration (i.e., hematocrit) begins to increase (beyond 1%), scattering begins to overtake absorption as the primary light extinction contributor, with some light absorbed by the hemoglobin present in each cell, but much more light (2-3 orders of magnitude) scattered from the surfaces of the red blood cells, leading to an increase in the intensity of the reflected light measured by the light detector 96 and the increasing intensity trend illustrated in FIG. 16.

Accordingly, the controller 98 is configured to determine that, if the redness in the subject fluid at the second time is greater than the redness in the fluid at the first time, the redness in the fluid is due to the presence of red blood cells if the second intensity is greater than the first intensity or due to the presence of free hemoglobin if the first intensity is greater than the second intensity. Conversely, if the redness in the biological fluid at the second time is less than the redness in the biological fluid at the first time, the controller 98 determines that the redness in the fluid is due to the presence of red blood cells if the second intensity is less than the first intensity or due to the presence of free hemoglobin if the first intensity is less than the second intensity. In any case, the controller 98 generates an output that is indicative of the cause of the redness in the subject fluid (i.e., either the presence of red blood cells or free hemoglobin), which may be used to modify the separation procedure or for any other purpose.

In one embodiment, while the differentiating optical sensor device 72 is configured to differentiate between redness caused by the presence of red blood cells or by the presence of free hemoglobin, it is not configured to determine the hematocrit or free hemoglobin concentration of the subject fluid. If it is desired to determine the hematocrit or free hemoglobin concentration of the subject fluid, the differentiating optical sensor device 72 may be used in combination with a separate device that is configured to determine hematocrit and/or free hemoglobin concentration (e.g., a hematocrit measurement device of the type described in U.S. Pat. No. 9,164,078 or a free hemoglobin concentration measurement device of the type described in U.S. Pat. No. 9,833,557).

In another embodiment, rather than providing a separate device to determine hematocrit and/or free hemoglobin concentration, the differentiating optical sensor device 72 may include this functionality. For example, if the differentiating optical sensor device 72 is configured according to the description of the colorimetric optical sensor device of U.S. Provisional Patent Application Ser. No. 62/657,397, it will be capable of determining the hematocrit or free hemoglobin concentration of the subject fluid. In such an embodiment, the light source 94 is provided as a broadband light source, while the light detector 96 is provided as an optical spectrometer, as described above. Such a differentiating optical sensor device 72 operates according to the foregoing description, with light from the light source 94 reflecting back from the subject fluid, to be at least partially received by the light detector 96. The reflected light that is received by the light detector 96 has a plurality of wavelengths, with the light detector 96 (as an optical spectrometer) being configured for measurement and wavelength differentiation of at least a portion of the reflected light that it receives.

Figure 18:
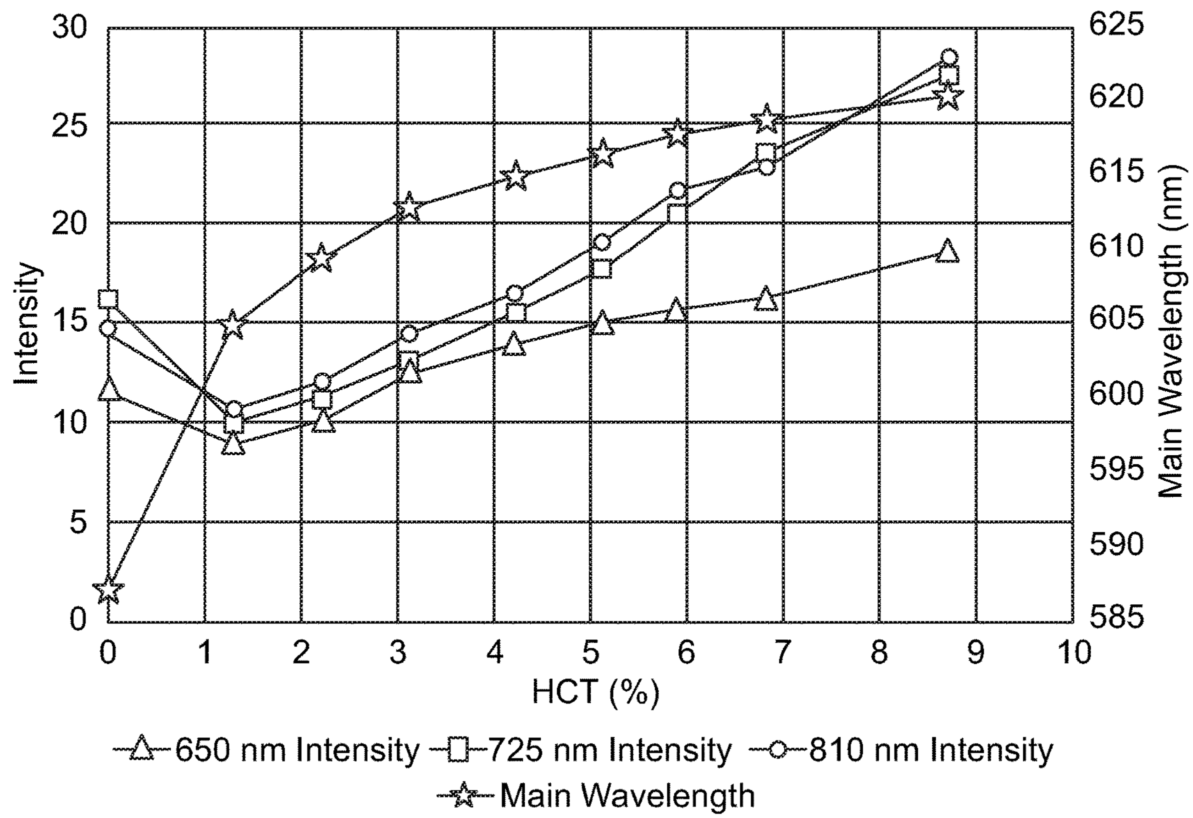
FIG. 18 is a variation of the chart of FIG. 16, further showing the relationship between hematocrit and the intensity of reflected light for the main wavelength of light reflected by a fluid.
Figure 19:
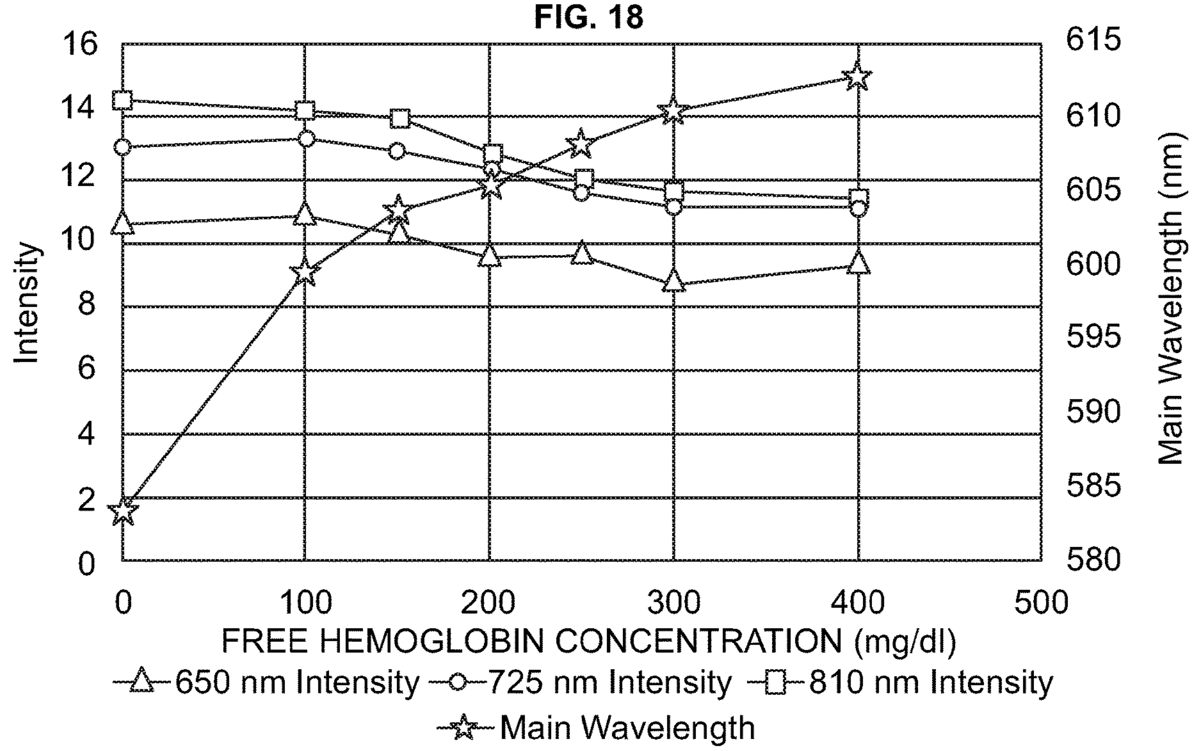
FIG. 19 is a variation of the chart of FIG. 17, further showing the relationship between free hemoglobin concentration and the intensity of reflected light for the main wavelength of light reflected by a fluid.

The light detector 96 (as an optical spectrometer) analyzes at least a portion of the received light and differentiates the wavelengths contained within the light to produce an optical spectrum of the light. A main wavelength is then determined from the optical spectrum, such as by using a conventional color specification system, which may be software of the type marketed by Thorlabs, Inc. FIGS. 18 and 19 are modified versions of FIGS. 16 and 17, respectively, which supplement the original versions by further showing the relationship between the intensity of the reflected light received by the light detector 96 at the main wavelength and hematocrit (FIG. 18) or free hemoglobin concentration (FIG. 19).

As described above, a differentiating optical sensor device 72 having colorimetric capabilities is capable of assessing a change in redness between the first and second times, which may be done by the controller 98 comparing the main wavelength at the first time to the main wavelength at the second time. If the main wavelength at the second time is greater than the main wavelength at the first time, that is indicative of an increase in redness in the subject fluid, whereas a decrease in the main wavelength from the first time to the second time is indicative of a decrease in redness in the subject fluid.

When the main wavelength has been determined, the controller 98 then correlates the main wavelength to a corresponding hematocrit or free hemoglobin concentration, which may be experimentally determined. A particular main wavelength may correspond to a particular hematocrit and to a particular free hemoglobin concentration, so it may be advantageous for the controller 98 to first determine whether redness in the subject fluid is due to the presence of red blood cells or free hemoglobin before matching the main wavelength to a particular hematocrit or free hemoglobin concentration.

When the controller 98 has correlated the main wavelength to a corresponding hematocrit or free hemoglobin concentration, it may generate an output that is indicative of that value. The output of the controller 98 may be directed to the interface command module 88 or some other module of the interface controller to control separation of the biological fluid or may be put to some other use.

The correlation between main wavelength and hematocrit may be greater between 0% and 20% than above 20%, so the best results may be achieved when applying the hematocrit measurement principles to fluid having (or intended to have) a relatively low hematocrit (e.g., plasma or other supernatant, buffy coat, MNC-containing layer, and other cellular components with a low red blood cell content) rather than a higher hematocrit (e.g., whole blood and packed red cells). However, it should be understood that the hematocrit measurement principles of this embodiment may be employed for fluids having a relatively high hematocrit. In these cases, it may be advantageous for the subject fluid to comprise a diluted fluid, which has been diluted from an undiluted or less diluted condition of interest to reduce the hematocrit (preferably to a level below 20%). The main wavelength and hematocrit of the (diluted) fluid are determined, as described above. Then, the hematocrit of the fluid of interest (i.e., the fluid in its undiluted or less diluted state) may be determined, followed by the controller 98 generating an alternative or additional output that is indicative of the hematocrit of the fluid of interest. Alternatively, if the controller 98 determines that the subject fluid has a hematocrit greater than 20%, it may disable the hematocrit measurement functionality and generate an alert to the operator.

D. Fluid Flow Circuit

FIG. 12 shows an exemplary fluid flow circuit 12 that may be used in carrying out the red blood cell and free hemoglobin differentiation principles described herein. The illustrated fluid flow circuit 12 has a "two needle" configuration, which includes a pair of fluid source access devices 120 and 122 (e.g., phlebotomy needles) configured for direct connection to a fluid source. The fluid source access devices 120 and 122 are connected by tubing 124 and 126 (referred to herein as a draw line and a return line, respectively) to a first or left cassette 128*a*. One of the fluid source access devices 120 is used to draw fluid (e.g., blood in an MNC collection procedure) from the fluid source into the fluid flow circuit 12 and is connected to the left cassette 128*a* through a y-connector 130. The other leg of the y-connector 130 is connected to tubing 132 which leads to a second or middle cassette 128*b*. The tubing 132 is connected, through the middle cassette 128*b*, to additional tubing 134, which includes a container access device 136 (e.g., a sharpened cannula or spike connector) for accessing the interior of a container, which may be an anticoagulant container in the case of a blood treatment operation. During a blood treatment operation (e.g., an MNC collection procedure), anticoagulant from the anticoagulant container is added to the blood from the fluid source at the y-connector 130 prior to entering the left cassette 128*a*.

The other fluid source access device 122 is used to deliver or return the original drawn fluid, a component of that fluid, and/or some other fluid to the fluid source (or to some other fluid recipient) and is also connected to the left cassette 128*a* through a y-connector 138. The other leg of the y-connector 138 is connected to tubing 140 in fluid communication at its other end with a container access device 142. Although not illustrated, the container access device 142 may be associated with a container having an amount of fluid (e.g., saline) to be used to prime the fluid flow circuit 12 and/or delivered to the fluid source (or some other fluid recipient) via the fluid source access device 122.

The left cassette 128*a* is also connected to tubing 144 in fluid communication with the separation chamber 22, which separates the fluid into its constituent parts and returns the fluid components to the fluid flow circuit 12, as described above. One of the fluid components (which may be separated red blood cells in an MNC collection procedure) is conveyed to the middle cassette 128*b* from the separation chamber 22 via tubing 146, while another separated component (which may be a plasma constituent in an MNC collection procedure) is conveyed to a third or right cassette 128*c* of the fluid flow circuit 12 from the separation chamber 22 via tubing 94. The first separated component (e.g., red blood cells) may be pumped to the left cassette 128*a* via tubing 148, where it is returned to the fluid source (or to some other fluid recipient), or may instead exit the middle cassette 128*b* via tubing 150 to a collection container 152 (referred to as a red blood cell collection container, in the context of a blood separation procedure) for storage or later use or may be recirculated from the middle cassette 128*b* through the separation chamber 22, as described above. The second separated component (e.g., the plasma constituent) may be pumped back to the left cassette 128*a* via tubing 154 for return to the fluid source (or to some other fluid recipient) and/or it may be pumped into a collection container 156 (referred to as a plasma collection container, in the context of a blood separation procedure) via different tubing 158 or recirculated from the right cassette 128*c* through the separation chamber 22, as described above. The destination of the various fluids passing through the cassettes depends upon the actuation of the various valves of the cassettes 128, as described in greater detail in U.S. Pat. No. 5,462,416, which is incorporated herein by reference.

Each illustrated cassette 128 includes an injection-molded body that is compartmentalized by an interior wall to present or form a topside (which faces away from the separation assembly 10, during use) and an underside (which faces toward the separation assembly 10, during use). A flexible diaphragm overlies and peripherally seals the underside of each cassette 128, while a generally rigid upper panel overlies the topside of each cassette 128 and is sealed peripherally and to raised, channel-defining walls in the cassette 128.

The top- and undersides of the cassettes 128 contain preformed cavities. On the underside of the cassettes 128, the cavities form an array of valve stations and an array of pressure sensing stations. On the topside of the cassettes 128, the cavities form an array of channels or paths for conveying fluids. The valve stations communicate with the flow paths through the interior wall to interconnect them in a predetermined manner. The sensing stations also communicate with the flow paths through the interior wall to sense pressures in selected regions. The number and arrangement of the flow paths, the valve stations, and the sensing stations can vary without departing from the scope of the present disclosure.

In the illustrated embodiment, ten pre-molded tube connectors extend out along opposite side edges of each cassette 128. The tube connectors are arranged five on one side edge and five on the other side edge. The other side edges of the cassettes 128, as illustrated, are free of tube connectors. The tube connectors are associated with external tubing to associate the cassettes 128 with the remainder of the fluid flow circuit 12 (e.g., to a plasma collection container 156, an MNC collection container 160, or a red blood cell collection container 152) or to define tubing loops 162 that interact with pumps 90 of the separation assembly 10 to convey fluid through the fluid flow circuit 12, as described in greater detail in U.S. Pat. No. 5,462,416.

The tube connectors communicate with various interior flow paths, which constitute the flow paths of the cassettes 128 through which a fluid enters or exits the cassette 128. The remaining interior flow paths of the cassette 128 constitute branch paths that link the flow paths associated with the tube connectors to each other through the valve stations and sensing stations. The particular configuration of one suitable cassette is described in greater detail in U.S. Pat. No. 5,462,416.

The fluid flow circuit 12 may also include a number of other components, including clamps or valves, an air detector 164, and a drip chamber 166 that fluid passes through before entering the separation chamber 22.

As described above, the differentiating optical sensor device 72 may be oriented to monitor fluid in any optically appropriate portion or vessel of the fluid flow circuit 12 (i.e., any portion or vessel in which fluid may be present and which is configured to allow for the passage of broadband light, with the fluid therein being subject to a possible change in redness). This may include one of the tubes or conduits through which fluid flows, one of the cassettes, one of the containers, and the separation chamber 22. Additionally, the separation assembly 10 may include a plurality of differentiating optical sensor devices 72, with each one being configured to be associated with a different portion or vessel of the fluid flow circuit 12. Finally, it should be understood that the red blood cell and free hemoglobin differentiation principles described herein are not limited to monitoring of any particularly configured extracorporeal biological fluid flow circuit, but may be applied to any fluid flow circuit having an optically appropriate portion or vessel or to any other optically appropriate vessel in which redness in a biological fluid is capable of changing.

Aspects

Aspect 1. A method of determining a cause of redness in a biological fluid, comprising: exposing a biological fluid to a light including a wavelength in a range of 650 nm to 900 nm at a first time and at a second time that is subsequent to the first time so as to cause at least a portion of the light to be reflected by the biological fluid; receiving at least a portion of the reflected light at the first time and at the second time; analyzing at least a portion of the received light at the first time to determine a first intensity of said at least a portion of the received light at said wavelength and at the second time to determine a second intensity of said at least a portion of the received light at said wavelength; determining whether the redness in the biological fluid at the second time is greater or less than the redness in the biological fluid at the first time; comparing the first intensity to the second intensity; and generating an output indicative of a presence of red blood cells in the biological fluid or generating an output indicative of a presence of free hemoglobin in the biological fluid, based upon said determination of whether the redness in the biological fluid at the second time is greater or less than the redness in the biological fluid at the first time and upon said comparison of the first intensity to the second intensity.

Aspect 2. The method of Aspect 1, wherein the output is indicative of the presence of red blood cells in the biological fluid when the redness in the biological fluid at the second time is greater than the redness in the biological fluid at the first time and the second intensity is greater than the first intensity or when the redness in the biological fluid at the second time is less than the redness in the biological fluid at the first time and the second intensity is less than the first intensity, and the output is indicative of the presence of free hemoglobin in the biological fluid when the redness in the biological fluid at the second time is greater than the redness in the biological fluid at the first time and the first intensity is greater than the second intensity or when the redness in the biological fluid at the second time is less than the redness in the biological fluid at the first time and the first intensity is less than the second intensity.

Aspect 3. The method of any one of the preceding Aspects, wherein the first time comprises a time at which the biological fluid is first exposed to the light.

Aspect 4. The method of any one of the preceding Aspects, wherein the biological fluid comprises a separated blood component.

Aspect 5. The method of any one of the preceding Aspects, wherein the biological fluid comprises platelet-poor plasma, platelet-rich plasma, or mononuclear cells.

Aspect 6. The method of any one of the preceding Aspects, wherein the biological fluid is exposed to light from a broadband light source.

Aspect 7. The method of Aspect 6, wherein the light from the broadband light source includes at least all wavelengths in the visible range.

Aspect 8. The method of any one of Aspects 1-5, wherein the biological fluid is exposed to light from a single wavelength light source.

Aspect 9. The method of any one of the preceding Aspects, wherein the biological fluid is present in a vessel, the light to which the biological fluid is to be exposed is transmitted through a surface of the vessel prior to the biological fluid being exposed to the light, and the light to which the biological fluid is to be exposed strikes the surface of the vessel at an angle.

Aspect 10. The method of Aspect 9, wherein the angle is between 30° and 60°.

Aspect 11. The method of Aspect 9, wherein the angle is approximately 45°.

Aspect 12. The method of any one of the preceding Aspects, wherein the light to which the biological fluid is to be exposed is transmitted through a transmitting optical fiber prior to the biological fluid being exposed to the light, and/or said at least a portion of the reflected light is transmitted through a receiving optical fiber before being analyzed.

Aspect 13. The method of any one of the preceding Aspects, wherein the light to which the biological fluid is to be exposed is transmitted through a plurality of transmitting optical fibers prior to the biological fluid being exposed to the light, said at least a portion of the reflected light is transmitted through a receiving optical fiber before being analyzed, and the receiving optical fiber is centrally located with respect to said plurality of transmitting optical fibers.

Aspect 14. The method of any of the preceding Aspects, wherein said determining whether the redness in the biological fluid at the second time is greater or less than the redness in the biological fluid at the first time comprises determining a main wavelength of said at least a portion of the received light at the first time and at the second time, comparing the main wavelength of said at least a portion of the received light at the first time to the main wavelength of said at least a portion of the received light at the second time, determining that the redness in the biological fluid at the second time is greater than the redness in the biological fluid at the first time when the main wavelength is greater at the second time than at the first time, and determining that the redness in the biological fluid at the second time is less than the redness in the biological fluid at the first time when the main wavelength is greater at the first time than at the second time.

Aspect 15. An optical sensor device comprising: a light source configured to emit a light including a wavelength in a range of 650 nm to 900 nm, with at least a portion of the light being exposed to a biological fluid and reflected at a first time and at a second time that is subsequent to the first time; a light detector configured to receive at least a portion of the reflected light and analyze at least a portion of the received light at the first time to determine a first intensity of said at least a portion of the received light at said wavelength and at the second time to determine a second intensity of said at least a portion of the received light at said wavelength; and a controller configured to compare the first intensity to the second intensity and generate an output indicative of a presence of red blood cells in the biological fluid or generate an output indicative of a presence of free hemoglobin in the biological fluid, based upon whether the redness in the biological fluid at the second time is greater or less than the redness in the biological fluid at the first time and upon said comparison of the first intensity to the second intensity.

Aspect 16. The optical sensor device of Aspect 15, wherein the output is indicative of the presence of red blood cells in the biological fluid when the redness in the biological fluid at the second time is greater than the redness in the biological fluid at the first time and the second intensity is greater than the first intensity or when the redness in the biological fluid at the second time is less than the redness in the biological fluid at the first time and the second intensity is less than the first intensity, and the output is indicative of the presence of free hemoglobin in the biological fluid when the redness in the biological fluid at the second time is greater than the redness in the biological fluid at the first time and the first intensity is greater than the second intensity or when the redness in the biological fluid at the second time is less than the redness in the biological fluid at the first time and the first intensity is less than the second intensity.

Aspect 17. The optical sensor device of any one of Aspects 15-16, wherein the first time comprises a time at which the biological fluid is first exposed to the light.

Aspect 18. The optical sensor device of any one of Aspects 15-17, wherein the biological fluid comprises a separated blood component.

Aspect 19. The optical sensor device of any one of Aspects 15-18, wherein the biological fluid comprises platelet-poor plasma, platelet-rich plasma, or mononuclear cells.

Aspect 20. The optical sensor device of any one of Aspects 15-19, wherein the light source comprises a broadband light source.

Aspect 21. The optical sensor device of Aspect 20, wherein the light from the broadband light source includes at least all wavelengths in the visible range.

Aspect 22. The optical sensor device of any one of Aspects 15-19, wherein the light source comprises a single wavelength light source.

Aspect 23. The optical sensor device of any one of Aspects 15-22, wherein the biological fluid is present in a vessel, the light emitted by the light source is configured to be transmitted through a surface of the vessel prior to the biological fluid being exposed to the light, and the light emitted by the light source is configured to strike the surface of the vessel at an angle.

Aspect 24. The optical sensor device of Aspect 23, wherein the angle is between 30° and 60°.

Aspect 25. The optical sensor device of Aspect 23, wherein the angle is approximately 45°.

Aspect 26. The optical sensor device of any one of Aspects 15-25, further comprising a transmitting optical fiber through which the light emitted by the light source is transmitted before being exposed to the biological fluid, and/or a receiving optical fiber through which said at least a portion of the reflected light is transmitted before being received by the light detector.

Aspect 27. The optical sensor device of any one of Aspects 15-26, further comprising an optical fiber bundle including a plurality of transmitting optical fibers through which the light emitted by the light source is transmitted before being exposed to the biological fluid, and a receiving optical fiber through which said at least a portion of the reflected light is transmitted before being received by the light detector, wherein the receiving optical fiber is centrally located with respect to said plurality of transmitting optical fibers.

Aspect 28. The optical sensor device of any one of Aspects 15-27, wherein the light detector comprises an optical spectrometer configured to receive at least a portion of the reflected light and analyze at least a portion of the received light to determine a main wavelength of said at least a portion of the received light at the first time and at the second time, and the controller is configured to compare the main wavelength of said at least a portion of the received light at the first time to the main wavelength of said at least a portion of the received light at the second time, determine that the redness in the biological fluid at the second time is greater than the redness in the biological fluid at the first time when the main wavelength is greater at the second time than at the first time, and determine that the redness in the biological fluid at the second time is less than the redness in the biological fluid at the first time when the main wavelength is greater at the first time than at the second time.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method of discerning between the presence of red blood cells and free hemoglobin in a biological fluid, comprising:

exposing a biological fluid to a light including a plurality of wavelengths, including at least one wavelength in a range of 650 nm to 900 nm at a first time and at a second time that is subsequent to the first time so as to cause at least a portion of the light to be reflected by the biological fluid;

receiving at least a portion of the reflected light at the first time and at the second time;

analyzing at least a portion of the received light at the first time to determine a first main wavelength of said at least a portion of the received light and a first intensity of said at least a portion of the received light at one of said plurality of wavelengths;

analyzing at least a portion of the received light at the second time to determine a second main wavelength of said at least a portion of the received light and a second intensity of said at least a portion of the received light at said one of said plurality of wavelengths;

determining whether the second main wavelength is longer or shorter than the first main wavelength;

comparing the first intensity to the second intensity; and generating an output indicative of a presence of red blood cells in the biological fluid or generating an output indicative of a presence of free hemoglobin in the biological fluid, based upon said determination of whether the second main wavelength is longer or shorter than the first main wavelength and upon said comparison of the first intensity to the second intensity.

2. The method of claim 1, wherein the output is indicative of the presence of red blood cells in the biological fluid when the second main wavelength is longer than the first main wavelength and the second intensity is greater than the first intensity or when the second main wavelength is shorter than the first main wavelength and the second intensity is less than the first intensity, and the output is indicative of the presence of free hemoglobin in the biological fluid when the second main wavelength is longer than the first main wavelength and the first intensity is greater than the second intensity or when the second main wavelength is shorter than the first main wavelength and the first intensity is less than the second intensity.

3. The method of claim 1, wherein the first time comprises a time at which the biological fluid is first exposed to the light.

4. The method of claim 1, wherein the biological fluid comprises a separated blood component.

5. The method of claim 1, wherein the biological fluid comprises platelet-poor plasma, platelet-rich plasma, or mononuclear cells.

6. The method of claim 1, wherein the biological fluid is exposed to light from a broadband light source.

7. The method of claim 6, wherein the light from the broadband light source includes at least all wavelengths in the visible range.

8. The method of claim 1, wherein the biological fluid is present in a vessel, the light to which the biological fluid is to be exposed is transmitted through a surface of the vessel prior to the biological fluid being exposed to the light, and the light to which the biological fluid is to be exposed strikes the surface of the vessel at an angle.

9. An optical sensor device comprising:

a light source configured to emit a light including a plurality of wavelengths, including at least one wavelength in a range of 650 nm to 900 nm, with at least a portion of the light being exposed to a biological fluid and reflected at a first time and at a second time that is subsequent to the first time;

a light detector configured to receive at least a portion of the reflected light and analyze at least a portion of the received light at the first time to determine a first main wavelength of said at least a portion of the received light and a first intensity of said at least a portion of the received light at one of said plurality of wavelengths and at the second time to determine a second main wavelength of said at least a portion of the received light and a second intensity of said at least a portion of the received light at said one of said plurality of wavelengths; and a controller configured to compare the first intensity to the second intensity and generate an output indicative of a presence of red blood cells in the biological fluid or generate an output indicative of a presence of free hemoglobin in the biological fluid, based upon whether the second main wavelength is longer or shorter than the first main wavelength and upon said comparison of the first intensity to the second intensity.

10. The optical sensor device of claim 9, wherein the output is indicative of the presence of red blood cells in the biological fluid when the second main wavelength is longer than the first mainwavelength and the second intensity is greater than the first intensity or when the second main wavelength is shorter than the first main wavelength and the second intensity is less than the first intensity, and the output is indicative of the presence of free hemoglobin in the biological fluid when the second main wavelength is longer than the first main wavelength and the first intensity is greater than the second intensity or when the second main wavelength is shorter than the first main wavelength and the first intensity is less than the second intensity.

11. The optical sensor device of claim 9, wherein the first time comprises a time at which the biological fluid is first exposed to the light.

12. The optical sensor device of claim 9, wherein the biological fluid comprises a separated blood component.

13. The optical sensor device of claim 9, wherein the biological fluid comprises platelet-poor plasma, platelet-rich plasma, or mononuclear cells.

14. The optical sensor device of claim 9, wherein the light source comprises a broadband light source.

15. The optical sensor device of claim 14, wherein the light from the broadband light source includes at least all wavelengths in the visible range.

16. The optical sensor device of claim 9, wherein the biological fluid is present in a vessel, the light emitted by the light source is configured to be transmitted through a surface of the vessel prior to the biological fluid being exposed to the light, and the light emitted by the light source is configured to strike the surface of the vessel at an angle.

17. The optical sensor device of claim 16, wherein the angle is between 30° C. and 60° C.

18. The optical sensor device of claim 16, wherein the angle is approximately 45° C.

19. The optical sensor device of claim 9, further comprising a transmitting optical fiber through which the light emitted by the light source is transmitted before being exposed to the biological fluid, and/or a receiving optical fiber through which said at least a portion of the reflected light is transmitted before being received by the light detector.

20. The optical sensor device of claim 9, further comprising an optical fiber bundle including a plurality of transmitting optical fibers through which the light emitted by the light source is transmitted before being exposed to the biological fluid, and a receiving optical fiber through which said at least a portion of the reflected light is transmitted before being received by the light detector, wherein the receiving optical fiber is centrally located with respect to said plurality of transmitting optical fibers.

* * * * *